(12) United States Patent
Blotsky et al.

(10) Patent No.: US 9,107,869 B2
(45) Date of Patent: *Aug. 18, 2015

(54) ANTI-GLYCATION METHODS AND COMPOSITIONS

(71) Applicant: CORE INTELLECTUAL PROPERTIES HOLDINGS, LLC, Goodyear, AZ (US)

(72) Inventors: Roger Blotsky, Goodyear, AZ (US); Ramon Figueroa, Miami, FL (US); Krys Bojanowski, Santa Paula, CA (US); Reynold Dominguez, Miami, FL (US)

(73) Assignee: CORE INTELLECTUAL PROPERTIES HOLDINGS, LLC, Goodyear, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/553,420

(22) Filed: Nov. 25, 2014

(65) Prior Publication Data

US 2015/0150909 A1     Jun. 4, 2015

Related U.S. Application Data

(63) Continuation of application No. 12/249,798, filed on Oct. 10, 2008, now Pat. No. 8,927,031.

(60) Provisional application No. 61/079,826, filed on Jul. 11, 2008, provisional application No. 60/998,316, filed on Oct. 10, 2007.

(51) Int. Cl.
| | |
|---|---|
| *A61K 36/00* | (2006.01) |
| *A61K 35/08* | (2015.01) |
| *A61K 33/42* | (2006.01) |
| *A61K 33/06* | (2006.01) |
| *A61K 33/20* | (2006.01) |
| *A61K 33/00* | (2006.01) |
| *A61K 33/24* | (2006.01) |
| *A23L 1/304* | (2006.01) |
| *A23L 2/52* | (2006.01) |

(52) U.S. Cl.
CPC .................. *A61K 35/08* (2013.01); *A23L 1/304* (2013.01); *A23L 2/52* (2013.01); *A61K 33/00* (2013.01); *A61K 33/06* (2013.01); *A61K 33/20* (2013.01); *A61K 33/24* (2013.01); *A61K 33/42* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 3,092,111 | A | 6/1963 | Saperstein et al. |
| 3,617,215 | A | 11/1971 | Sugahara et al. |
| 3,990,885 | A | 11/1976 | Baillie et al. |
| 4,150,093 | A | 4/1979 | Kaminsky et al. |
| 4,163,800 | A | 8/1979 | Wickett |
| 4,299,826 | A | 11/1981 | Luedders |
| 4,533,459 | A | 8/1985 | Dente et al. |
| 4,904,627 | A | 2/1990 | Bhattacharyya |
| 5,935,584 | A | 8/1999 | Guerrero et al. |
| 5,939,085 | A | 8/1999 | Jacobs et al. |
| 6,042,839 | A | 3/2000 | Lahanas et al. |
| 6,294,179 | B1 | 9/2001 | Lee et al. |
| 6,432,430 | B1 | 8/2002 | Fitzjarrell |
| 6,764,991 | B2 | 7/2004 | Puvvada et al. |
| 7,074,565 | B2 | 7/2006 | Dunbar |
| 7,575,772 | B2 | 8/2009 | Shi et al. |
| 8,709,497 | B2 | 4/2014 | Blotsky et al. |
| 8,927,031 | B2 | 1/2015 | Blotsky et al. |
| 2002/0069685 | A1 | 6/2002 | Adam |
| 2003/0049225 | A1 | 3/2003 | Rucker |
| 2003/0108624 | A1 | 6/2003 | Kosbab |
| 2003/0224028 | A1 | 12/2003 | Galey |
| 2004/0081712 | A1 | 4/2004 | Hermansen |
| 2004/0161435 | A1 | 8/2004 | Gupta |
| 2004/0258597 | A1 | 12/2004 | Michalakos et al. |
| 2006/0093685 | A1 | 5/2006 | Mower et al. |
| 2007/0031462 | A1 | 2/2007 | Blotsky et al. |
| 2007/0082106 | A1 | 4/2007 | Lee et al. |
| 2007/0116832 | A1 | 5/2007 | Prakash |
| 2007/0148186 | A1 | 6/2007 | Ketzis |
| 2007/0190173 | A1 | 8/2007 | Blotsky et al. |
| 2009/0226545 | A1 | 9/2009 | Blotsky et al. |

(Continued)

FOREIGN PATENT DOCUMENTS

| | | |
|---|---|---|
| EP | 2207420 | 7/2010 |
| JP | 2001294896 | 10/2001 |

(Continued)

OTHER PUBLICATIONS

Ames BN, Shigenaga MK, Hagen TM. (1993) Oxidants, antioxidants, and the degenerative diseases of aging. Proc Natl Acad Sci USA. 90(17): 7915-7922.

Anjos S, Polychronakos C. (2004) Mechanisms of genetic susceptibility to type I diabetes: beyond HLA. Mol. Gen. Metabolism, 81: 187-195.

(Continued)

*Primary Examiner* — Qiuwen Mi
(74) *Attorney, Agent, or Firm* — Ballard Spahr LLP

(57) ABSTRACT

The present invention comprises compositions that provide anti-glycation activity comprising a mineral extract composition or a mogroside/mineral extract composition or a mogroside composition. Such compositions are useful for methods of preventing, treating and inhibiting the effects of glycation in the body. The methods of the present invention comprise use of anti-glycation composition for the treatment and prevention of glycation related conditions including diabetes, atherosclerosis, arthritis, mental conditions and vision impairment.

13 Claims, 7 Drawing Sheets

(56) References Cited

U.S. PATENT DOCUMENTS

| | | | |
|---|---|---|---|
| 2010/0129465 A1 | 5/2010 | Blotsky et al. | |
| 2014/0314683 A1 | 10/2014 | Blotsky et al. | |

FOREIGN PATENT DOCUMENTS

| | | |
|---|---|---|
| WO | WO 2007/149410 | 12/2007 |
| WO | WO 2009/023975 | 2/2009 |
| WO | WO 2009/049246 | 4/2009 |

OTHER PUBLICATIONS

Bahram et al. (2008) Genetics of type 2 diabetes mellitus and obesity—a review. Annals Medicine, 40: 2-10.

Blando F, Gerardi C, Nicoletti I. (2004) Sour Cherry (*Prunus cerasus* L) Anthocyanins as Ingredients for Functional Foods. J Biomed Biotechnol. 2004(5): 253-258.

Dignan P. (1981) Teratogenic Risk and Counseling in Diabetes. Clin Obstet Gynecol., 24(1): 149-159.

Field LL. (2002) Genetic linkage and association studies of Type I diabetes: challenges and rewards. Diabetologia, 45 (1):21-35.

Greiner DL, Rossini AA, Mordes JP. (2001) Translating data from animal models into methods for preventing human autoimmune diabetes mellitus: caveat emptor and primum non nocere. Clin Immunol., 100(2): 134-143.

Ikegami H, Fujisawa T, Ogihara T. (2004) Mouse models of type 1 and type 2 diabetes derived from the same closed colony: genetic susceptibility shared between two types of diabetes. ILAR J., 45(3): 268-277.

Li F, Wang CN, Zhou Y, Xiong WW. (2006) Analysis of contents of copper and cadmium in *Siraitia grosvenori*. Welling Yuansu Yu Jiankang Yanjiu, 23(6): 30-34.

Ou B, Hampsch-Woodill M, Prior RL. (2001) Development and validation of an improved oxygen radical absorbance capacity assay using fluorescein as the fluorescent probe. J Agric Food Chem. 49(10): 4619-4626.

Rahbar S, Figarola JL. (2002) Inhibitors and Breakers of Advanced Glycation Endproducts (AGEs): A Review. Curr. Med. Chem.—Imun., Endoc. & Metab. Agents, 2: 135-161.

Simpson RW, Shaw JE, Zimmet PZ. (2003) The prevention of type 2 diabetes—lifestyle change or pharmacotherapy? A challenge for the 21st century. Diabetes Res Clin Pract., 59(3): 165-180.

Stephen et al. (2009) Recent progress in the genetics of diabetes. Horm Res., 71 (Supp 1): 17-23.

Suzuki YA, Murata Y, Inui H, Sugiura M, Nakano Y. (2005) Triterpene glycosides of *Siraitia grosvenori* inhibit rat intestinal maltase and suppress the rise in blood glucose level after a single oral administration of maltose in rats. J Agric Food Chem., 53(8): 2941-2946.

Wicker LS, Moule CL, Fraser H, Penha-Goncalves C, Rainbow D, Garner VE, Chamberlain G, Hunter K, Howlett S, Clark J, Gonzalez-Munoz A, Cumiskey AM, Tiffen P, Howson J, Healy B, Smink LJ, Kingsnorth A, Lyons PA, Gregory S, Rogers J, Todd JA, Peterson LB. (2005) Natural genetic variants influencing type 1 diabetes in humans and in the NOD mouse. Novartis Found Symp., 267: 57-65.

Xiangyang Q, Weijun C, Liegang L, Ping Y, Bijun X. (2006) Effect of a *Siraitia grosvenori* extract containing mogrosides on the cellular immune system of type 1 diabetes mellitus mice. Mol Nutr Food Res. 50(8): 732-738.

International Search Report mailed Jun. 13, 2008 for PCT/US2007/014229, which was filed Jun. 19, 2007 and published as WO 2007/149410 (Applicant—Blotsky et al.; Inventor—Blotsky et al.).

International Preliminary Report on Patentability and Written Opinion mailed Jun. 19, 2007 for PCT/US2007/014229, which was filed Jun. 21, 2006 and published as WO 2007/149410 (Applicant—Blotsky et al.; Inventor—Blotsky et al.).

International Search Report mailed Jan. 8, 2009 for PCT/US2008/079632, which was filed Oct. 10, 2008 and published as WO 2009/049246 (Applicant—Global Organics LLC; Inventor—Blotsky et al.).

International Preliminary Report on Patentability and Written Opinion mailed Apr. 13, 2010 for PCT/US2008/079632, which was filed Oct. 10, 2008 and published as WO 2009/049246 (Applicant—Global Organics LLC; Inventor—Blotsky et al.).

Extended European Search Report issued Dec. 9, 2010 for EP Application Serial No. 08838086.0, which was filed Oct. 10, 2008 and published as EP 2207420 (Applicant—Global Organics LLC; Inventor—Boltsky et al.).

Restriction Requirement mailed Apr. 12, 2007 for U.S. Appl. No. 10/725,729, filed Dec. 2, 2003 (Inventor—Blotsky et al.) (6 pages).

Response to Restriction Requirement filed May 31, 2007 for U.S. Appl. No. 10/725,729, filed Dec. 2, 2003 (Inventor—Blotsky et al.) (2 pages).

Non-Final Office Action mailed Jun. 14, 2007 for U.S. Appl. No. 10/725,729, filed Dec. 2, 2003 (Inventor—Blotsky et al.) (10 pages).

Response to Non-Final Office Action filed Sep. 14, 2007 for U.S. Appl. No. 10/725,729, filed Dec. 2, 2003 (Inventor—Blotsky et al.) (7 pages).

Restriction Requirement mailed Nov. 26, 2007 for U.S. Appl. No. 10/725,729, filed Dec. 2, 2003 (Inventor—Blotsky et al.) (5 pages).

Response to Restriction Requirement filed Jan. 28, 2008 for U.S. Appl. No. 10/725,729, filed Dec. 2, 2003 (Inventor—Blotsky et al.) (5 pages).

Final Office Action mailed Apr. 30, 2008 for U.S. Appl. No. 10/725,729, filed Dec. 2, 2003 (Inventor—Blotsky et al.) (11 pages).

Response to Final Office Action filed Sep. 30, 2008 for U.S. Appl. No. 10/725,729, filed Dec. 2, 2003 (Inventor—Blotsky et al.) (11 pages).

Notice of Non-Compliant Amendment mailed Jan. 9, 2009 for U.S. Appl. No. 10/725,729, filed Dec. 2, 2003 (Inventor—Boltsky et al.) (4 pages).

Response to Notice of Non-Compliant Amendment filed Jun. 23, 2009 for U.S. Appl. No. 10/725,729, filed Dec. 2, 2003 (Inventor—Blotsky et al.) (15 pages).

Examiner's Interview Summary mailed Jul. 1, 2009 for U.S. Appl. No. 10/725,729, filed Dec. 2, 2003 (Inventor—Blotsky et al.) (4 pages).

Supplemental Response to Notice of Non-Compliant Amendment filed Jul. 8, 2009 for U.S. Appl. No. 10/725,729, filed Dec. 2, 2003 (Inventor—Blotsky et al.) (12 pages).

Non-Final Office Action mailed Sep. 29, 2009 for U.S. Appl. No. 10/725,729, filed Dec. 2, 2003 (Inventor—Blotsky et al.) (11 pages).

Response to Non-Final Office Action filed Mar. 29, 2010 for U.S. Appl. No. 10/725,729, filed Dec. 2, 2003 (Inventor—Blotsky et al.) (13 pages).

Examiner's Interview Summary mailed May 25, 2010 for U.S. Appl. No. 10/725,729, filed Dec. 2, 2003 (Inventor—Blotsky et al.) (4 pages).

Final Office Action mailed Jun. 24, 2010 for U.S. Appl. No. 10/725,729, filed Dec. 2, 2003 (Inventor—Blotsky et al.) (11 pages).

Applicant's Response to Inteview Summary filed Jun. 25, 2010 for U.S. Appl. No. 10/725,729, filed Dec. 2, 2003 (Inventor—Blotsky et al.) (2 pages).

Response to Final Office Action filed Sep. 24, 2010 for U.S. Appl. No. 10/725,729, filed Dec. 2, 2003 (Inventor—Blotsky et al.) (14 pages).

Non-Final Office Action mailed Feb. 21, 2013 for U.S. Appl. No. 10/725,729, filed Dec. 2, 2003 (Inventor—Blotsky et al.) (12 pages).

Response to Non-Final Office Action filed May 21, 2013 for U.S. Appl. No. 10/725,729, filed Dec. 2, 2003 (Inventor—Blotsky et al.) (9 pages).

Final Office Action mailed Sep. 11, 2013 for U.S. Appl. No. 10/725,729, filed Dec. 2, 2003 (Inventor—Blotsky et al.) (8 pages).

Applicant—Initiated Interview Summary mailed Oct. 22, 2013 for U.S. Appl. No. 10/725,729, filed Dec. 2, 2003 (Inventor—Blotsky et al.) (3 pages).

Response to Final Office Action filed Nov. 8, 2013 for U.S. Appl. No. 10/725,729, filed Dec. 2, 2003 (Inventor—Blotsky et al.) (8 pages).

Notice of Allowance mailed Dec. 2, 2013 for U.S. Appl. No. 10/725,729, filed Dec. 2, 2003 (Inventor—Blotsky et al.) (11 pages).

Supplemental Notice of Allowance mailed Mar. 31, 2014 for U.S. Appl. No. 10/725,729, filed Dec. 2, 2003 (Inventor—Blotsky et al.) (2 pages).

Issue Notification mailed Apr. 9, 2014 for U.S. Appl. No. 10/725,729, filed Dec. 2, 2003 (Inventor—Blotsky et al.) (1 page).

(56) References Cited

OTHER PUBLICATIONS

Restriction Requirement mailed Mar. 8, 2007 for U.S. Appl. No. 11/472,536, filed Jun. 21, 2006 (Inventor—Blotsky et al.).
Response to Restriction Requirement filed May 14, 2007 for U.S. Appl. No. 11/472,536, filed Jun. 21, 2006 (Inventor—Blotsky et al.).
Non-Final Office Action mailed Jun. 15, 2007 for U.S. Appl. No. 11/472,536, filed Jun. 21, 2006 (Inventor—Blotsky et al.).
Response after Non-Final Action filed Sep. 17, 2007 for U.S. Appl. No. 11/472,536, filed Jun. 21, 2006 (Inventor—Blotsky et al.).
Final Office Action mailed Nov. 26, 2007 for U.S. Appl. No. 11/472,536, filed Jun. 21, 2006 (Inventor—Blotsky et al.).
Amendment after Final Office Action filed Jan. 28, 2008 for U.S. Appl. No. 11/472,536, filed Jun. 26, 2006 (Inventor—Blotsky et al.).
Advisory Action mailed Feb. 13, 2008 for U.S. Appl. No. 11/472,536, filed Jun. 21, 2006 (Inventor—Blotsky et al.).
Response after Final Action with Request for Continued Examination filed Mar. 27, 2008 for U.S. Appl. No. 11/472,536, filed Jun. 21, 2006 (Inventor—Blotsky et al.).
Restriction Requirement mailed Jun. 20, 2008 for U.S. Appl. No. 11/472,536, filed Jun. 21, 2006 (Inventor—Blotsky et al.).
Response to Restriction Requirement filed Nov. 20, 2008 for U.S. Appl. No. 11/472,536, filed Jun. 21, 2006 (Inventor—Blotsky et al.).
Non-Final Office Action mailed Feb. 5, 2009 for U.S. Appl. No. 11/472,536, filed Jun. 21, 2006 (Inventor—Blotsky et al.).
Response after Non-Final Action filed Jul. 6, 2009 for U.S. Appl. No. 11/472,536, filed Jun. 21, 2006 (Inventor—Blotsky et al.).
Final Office Action mailed Oct. 9, 2009 for U.S. Appl. No. 11/472,536, filed Jun. 21, 2006 (Inventor—Blotsky et al.).
Response after Final Action with Request for Continued Examination filed Feb. 9, 2010 for U.S. Appl. No. 11/472,536, filed Jun. 21, 2006 (Inventor—Blotsky et al.).
Non-Final Office Action mailed Feb. 19, 2010 for U.S. Appl. No. 11/472,536, filed Jun. 21, 2006 (Inventor—Blotsky et al.).
Examiner Interview Summary mailed May 25, 2010 for U.S. Appl. No. 11/472,536, filed Jun. 21, 2006 (Inventor—Blotsky et al.).
Response to Interview Summary filed Jun. 25, 2010 for U.S. Appl. No. 11/472,536, filed Jun. 21, 2006 (Inventor—Blotsky et al.).
Response after Non-Final Action filed Jul. 19, 2010 for U.S. Appl. No. 11/472,536, filed Jun. 21, 2006 (Inventor—Blotsky et al.).
Non-Final Office Action issued Oct. 27, 2010 for U.S. Appl. No. 11/472,536, filed Jun. 21, 2006 (Inventor—Blotsky et al.).
Response to Non-Final Office Action filed Mar. 28, 2011 for U.S. Appl. No. 11/472,536, filed Jun. 21, 2006 (Inventor—Blotsky et al.) (16 pages).
Final Office Action mailed Jun. 8, 2011 for U.S. Appl. No. 11/472,536, filed Jun. 21, 2006 (Inventor—Blotsky et al.) (15 pages).
Response to Final Office Action filed Nov. 8, 2011 for U.S. Appl. No. 11/472,536, filed Jun. 21, 2006 (Inventor—Blotsky et al.) (12 pages).
Summary of Examiner Interview mailed Dec. 5, 2013 for U.S. Appl. No. 11/472,536, filed Jun. 21, 2006 (Inventor—Blotsky et al.) (2 pages).
Non-Final Office Action mailed Dec. 17, 2013 for U.S. Appl. No. 11/472,536, filed Jun. 21, 2006 (Inventor—Blotsky et al.) (12 pages).
Notice of Abandonment mailed Jul. 3, 2014 for U.S. Appl. No. 11/472,536, filed Jun. 21, 2006 (Inventor—Blotsky et al.) (2 pages).
Non-Final Office Action mailed Oct. 4, 2007 for U.S. Appl. No. 11/638,311, filed Dec. 12, 2006 (Inventor—Blotsky et al.).
Response after Non-Final Action filed Feb. 4, 2008 for U.S. Appl. No. 11/638,311, filed Dec. 12, 2006 (Inventor—Blotsky et al.).
Restriction Requirement mailed Apr. 29, 2008 for U.S. Appl. No. 11/638,311, filed Dec. 12, 2006 (Inventor—Blotsky et al.).
Response to Restriction Requirement filed May 29, 2008 for U.S. Appl. No. 11/638,311, filed Dec. 12, 2006 (Inventor—Blotsky et al).
Notice of Information or Non-Responsive Amendment mailed Jul. 28, 2008 for U.S. Appl. No. 11/638,311, filed Dec. 12, 2006 (Inventor—Blotsky et al.).
Response to Restriction Requirement filed Aug. 1, 2008 for U.S. Appl. No. 11/638,311, filed Dec. 12, 2006 (Inventor—Blotsky et al.).
Final Office Action mailed Oct. 20, 2008 for U.S. Appl. No. 11/638,311, filed Dec. 12, 2006 (Inventor—Blotsky et al.).

Response after Final Action with Request for Continued Examination filed Apr. 20, 2009 for U.S. Appl. No. 11/638,311, filed Dec. 12, 2006 (Inventor—Blotsky et al.).
Non-Final Office Action mailed Jun. 19, 2009 for U.S. Appl. No. 11/638,311, filed Dec. 12, 2006 (Inventor—Blotsky et al.).
Response after Non-Final Action filed Dec. 21, 2009 for U.S. Appl. No. 11/638,311, filed Dec. 12, 2006 (Inventor—Blotsky et al.).
Final Office Action mailed Mar. 31, 2010 for U.S. Appl. No. 11/638,311, filed Dec. 12, 2006 (Inventor—Blotsky et al.).
Examiner Interview Summary mailed May 28, 2010 for U.S. Appl. No. 11/638,311, filed Dec. 12, 2006 (Inventor—Blotsky et al.).
Response to Interview Summary filed Jun. 25, 2010 for U.S. Appl. No. 11/638,311, filed Dec. 12, 2006 (Inventor—Blotsky et al.).
Response after Final Action with Request for Continued Examination filed Jul. 30, 2010 for U.S. Appl. No. 11/638,311, filed Dec. 12, 2006 (Inventor—Blotsky et al.).
Non-Final Office Action issued Oct. 27, 2010 for U.S. Appl. No. 11/638,311, filed Dec. 12, 2006 (Inventor—Blotsky et al.).
Response to Non-Final Office Action filed Mar. 28, 2011 for U.S. Appl. No. 11/638,311, filed Dec. 12, 2006 (Inventor—Blotsky et al.) (15 pages).
Final Office Action mailed Jun. 8, 2011 for U.S. Appl. No. 11/638,311, filed Dec. 12, 2006 (Inventor—Blotsky et al.) (16 pages).
Response to Final Office Action filed Nov. 8, 2011 for U.S. Appl. No. 11/638,311, filed Dec. 12, 2006 (Inventor—Blotsky et al.) (13 pages).
Summary of Examiner Interview mailed Dec. 5, 2013 for U.S. Appl. No. 11/638,311, filed Dec. 12, 2006 (Inventor—Blotsky et al.) (2 pages).
Non-Final Office Action mailed Dec. 16, 2013 for U.S. Appl. No. 11/638,311, filed Dec. 12, 2006 (Inventor—Blotsky et al.) (13 pages).
Notice of Abandonment mailed Jul. 2, 2014 for U.S. Appl. No. 11/638,311, filed Dec. 12, 2006 (Inventor—Blotsky et al.) (2 pages).
Preliminary Amendment filed Mar. 28, 2014 for U.S. Appl. No. 14/229,340, filed Mar. 28, 2014 (Inventor—Blotsky et al.) (4 pages).
Non-Final Office Action mailed Aug. 28, 2014 for U.S. Appl. No. 14/229,340, filed Mar. 28, 2014 (Inventor—Blotsky et al.) (11 pages).
Response to Non-Final Office Action filed Nov. 26, 2014 for U.S. Appl. No. 14/229,340, filed Mar. 28, 2014 (Inventor—Blotsky et al.) (8 pages).
Supplemental Response filed Jan. 8, 2015 for U.S. Appl. No. 14/229,340, filed Mar. 28, 2014 (Inventor—Blotsky et al.) (6 pages).
Notice of Allowance mailed Jan. 27, 2015 for U.S. Appl. No. 14/229,340, filed Mar. 28, 2014 (Inventor—Blotsky et al.) (8 pages).
Restriction Requirement mailed Dec. 15, 2009 for U.S. Appl. No. 12/249,798, filed on Oct. 10, 2008 (Inventor—Blotsky et al.) (8 pages).
Response to Restriction Requirement filed Feb. 11, 2010 for U.S. Appl. No. 12/249,798, filed Oct. 10, 2008 (Inventor—Blotsky et al.) (7 pages).
Non-Final Office Action mailed Apr. 9, 2010 for U.S. Appl. No. 12/249,798, filed Oct. 10, 2008 (Inventor—Blotsky et al.) (16 pages).
Response after Non-Final Action filed Jul. 9, 2010 for U.S. Appl. No. 12/249,798, filed Oct. 10, 2008 (Inventor—Blotsky et al.) (11 pages).
Final Office Action mailed Jul. 14, 2010 for U.S. Appl. No. 12/249,798, filed Oct. 10, 2008 (Inventor—Blotsky et al.) (13 pages).
Response to Final Office Action filed Oct. 14, 2010 for U.S. Appl. No. 12/249,798, filed Oct. 10, 2008 (Inventor—Blotsky et al.) (8 pages).
Non-Final Office Action mailed May 12, 2014 for U.S. Appl. No. 12/249,798, filed Oct. 10, 2008 (Inventor—Blotsky et al.) (8 pages).
Response to Non-Final Office Action filed Aug. 8, 2014 for U.S. Appl. No. 12/249,798, filed Oct. 10, 2008 (Inventor—Blotsky et al.) (7 pages).
Notice of Allowance mailed Aug. 25, 2014 for U.S. Appl. No. 12/249,798, filed Oct. 10, 2008 (Inventor—Blotsky et al.) (8 pages).
Issue Notification mailed Dec. 17, 2014 for U.S. No. 12/249,798, filed Oct. 10, 2008 (Inventor—Blotsky et al.) (1 page).
Requirement for Restriction/Election mailed Jun. 2, 2011 for U.S. Appl. No. 12/497,387, filed Jul. 2, 2009 (Inventor—Blotsky et al.) (9 pages).

(56) References Cited

OTHER PUBLICATIONS

Response to Requirement for Restriction/Election filed Dec. 2, 2011 for U.S. Appl. No. 12/497,387, filed Jul. 2, 2009 (Inventor—Blotsky et al.) (11 pages).

Non-Final Office Action mailed Dec. 27, 2011 for U.S. Appl. No. 12/497,387, filed Jul. 2, 2009 (Inventor—Blotsky et al.) (7 pages).

Response to Non-Final Office Action filed Mar. 26, 2012 for U.S. Appl. No. 12/497,387, filed Jul. 2, 2009 (Inventor—Blotsky et al.) (10 pages).

Non-Final Office Action mailed Aug. 1, 2012 for U.S. Appl. No. 12/497,387, filed Jul. 2, 2009 (Inventor—Blotsky et al.) (8 pages).

Notice of Abandonment mailed Feb. 19, 2013 for U.S. Appl. No. 12/497,387, filed Jul. 2, 2009 (Inventor—Blotsky et al.) (2 pages).

ANTI-GLYCATION METHODS AND COMPOSITIONS

RELATED APPLICATIONS

The present application is a continuation of and claims priority to U.S. patent application Ser. No. 12/249,798, filed Oct. 10, 2008, now U.S. Pat. No. 8,927,031, which claims the benefit of U.S. Provisional Patent Application Ser. No. 60/998,316, filed Oct. 10, 2007, and U.S. Provisional Patent Application Ser. No. 61/079,826, filed Jul. 11, 2008, each of which is incorporated herein in its entirety.

TECHNICAL FIELD

The present invention relates to compositions used to treat or prevent glycation events and related pathologies in humans and animals. More particularly, the invention relates to compositions having anti-glycation activities.

BACKGROUND OF THE INVENTION

Glycation or non-enzymatic glycosylation involves reaction of amino groups of proteins, lipids, or nucleic acids with sugar aldehyde or keto groups to produce modified amino groups and eventually forming advanced glycosylation endproducts (AGE). Glycation may be the first step in a series of slow reactions in the body known as Amadori reactions, Schiff base reactions, and Maillard reactions and lead to advanced glycation endproducts (AGEs). Although glycation is slow in vivo, the glycation products may be reactive, or may have long-lasting effects and the presence of AGE is related to ageing and pathological conditions. In physiological conditions where there is an abundance of sugar molecules available for reaction, such as those where sugar levels are elevated, e.g. diabetes, glycation effects may be more pronounced. Some AGEs are benign, but others are more reactive, and are implicated in many age-related chronic diseases such as, type II diabetes mellitus, cardiovascular diseases, Alzheimer's disease, cancer, peripheral neuropathy, and other sensory losses such as deafness and blindness. Glycation also plays a role in lipid and RNA/DNA modifications.

Glycated substances are eliminated from the body slowly, since the renal clearance factor is only about 30%. This fact is used to provide a method of testing for sugar levels in diabetics. Red blood cells have a lifespan of 120 days and are easily accessible for measurement of recent increased presence of glycating product. The glycated hemoglobin level, also known as HbA1c, is determined and indicates the level of glycation occurring in the person.

Currently, aminoguanidine is used to slow down glycation by reacting with sugars and blocking the Amadori reactions. Aminoguanidine can reduce both in vitro and in vivo glucose-derived AGE. Aminoguanidine, a nucleophilic hydrazine compound, is currently being studied for use as treatment for AGE complications in diabetes. Additional drugs that inhibit AGE formation or disrupt already formed AGEs (e.g., AGE-breakers) are also under active investigation. For example, a reversal of vascular inelasticity leading to improvement of systolic hypertension and severe heart failure has been reported with AGE-breakers.

Diabetes is a metabolic disorder caused by a deficiency of insulin and is generally diagnosed by an increased blood glucose level. The disorder is characterized by a reduced glucose uptake of the insulin-dependent tissues. The disorder can be controlled by insulin injections but the long-term complications for diabetics include pathologies in the eye (cataractogenesis and retinopathy), kidney (nephropathy), neurons (neuropathy) and blood vessels (angiopathy and atherosclerosis). Glycation plays a role in the pathologies associated with diabetes.

Studies have shown that AGE may have a role in the development of atherosclerosis. Monocytes have AGE specific receptors (RAGE) and respond when stimulated by releasing cytokines. Minor injury to the blood vessel wall may expose sub-endothelial AGE, promote the infiltration of monocytes and initiate the development of atherosclerotic lesions. Circulating lipoproteins can also undergo glycation, which are then taken up by endothelial cells at a faster rate than non-glycated lipoprotein.

Intake of compositions that can counteract the long-term effects of AGE formation and prevent or treat AGE-related pathologies would be beneficial. Providing such compounds in easily consumed products, such as beverages or sweetener compositions, would be useful in the prevention or treatment of glycation related conditions.

SUMMARY

The present invention comprises methods and compositions for glycation treatments and prevention. The compositions of the present invention comprise mineral extract compositions that are useful for inhibiting glycation reactions in humans or animals, and for preventing and treating glycation-related conditions. Compositions of the present invention comprise mineral extract compositions, mogroside/mineral extract compositions, and mogroside compositions as described herein. Methods of the present invention comprise methods of treating or preventing glycation-related conditions comprising providing an effective amount of a mineral extract composition, a mogroside/mineral extract composition or a mogroside composition to prevent or reduce glycation events occurring in a human or animal.

Mineral extract compositions, mogroside/mineral extract compositions and/or mogroside compositions are provided or administered to subjects, humans or animals, alone or in combination with other components, to form anti-glycation compositions. For example, a mineral extract composition, a mogroside/mineral extract composition or a mogroside composition of the present invention may be combined with a foodstuff or beverage to provide an anti-glycation composition that is consumed by the subject. Effective amounts of anti-glycation compositions, for example, inhibit the formation of glycation products such as AGEs, and prevent or treat conditions related to glycation events in the body. Such glycation-related conditions include, but are not limited to, diabetes mellitus, cardiovascular diseases, Alzheimer's disease, cancer, peripheral neuropathy, and other sensory losses such as deafness, renal dysfunction, and blindness. Compositions of the present invention comprise a mineral extract composition, a mogroside/mineral extract composition or a mogroside composition in combination with compounds or compositions that have a sweet taste or are perceived as being sweet tasting, to form anti-glycation sweetener compositions.

DETAILED DESCRIPTION

Figure 1:
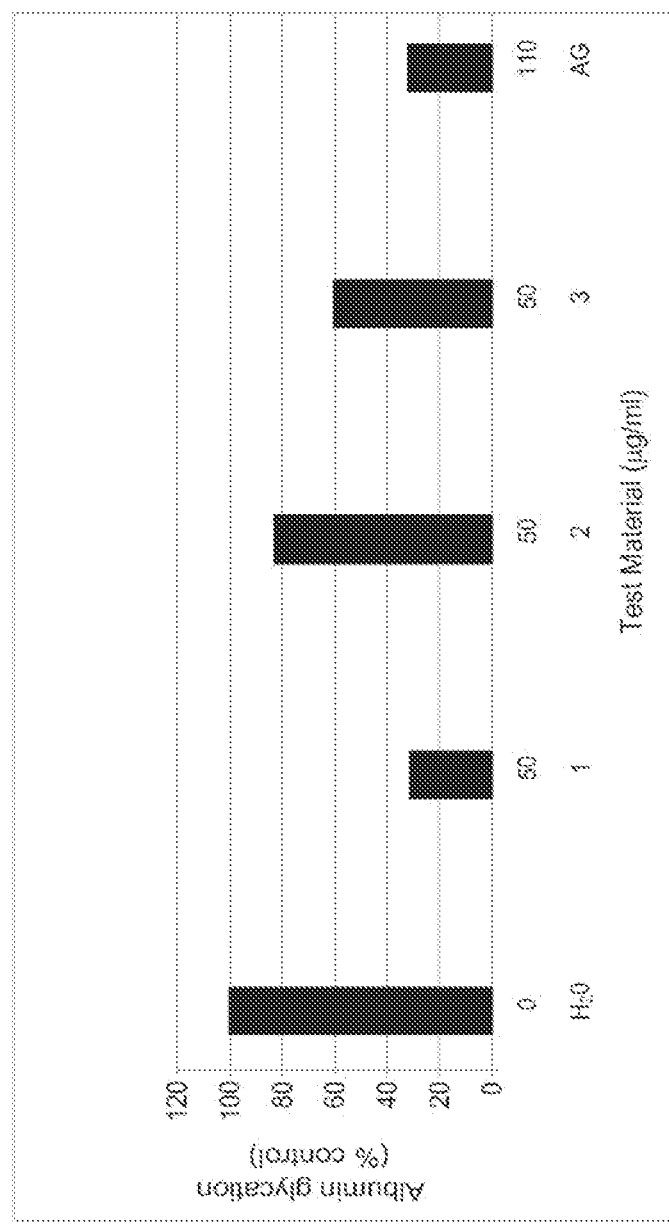
FIG. 1 is a graph showing the results of three mineral extract compositions in the anti-glycation assay.

The present invention comprises compositions and methods of treating or preventing complications and pathologies of conditions related to the presence of glycated molecules such as glycated proteins, lipids or nucleic acids. Glycation-related conditions comprise conditions in the bodies of humans or animals that are due to or related to the presence of glycated proteins, lipids, and nucleic acids, and include, but are not limited to, inflammatory responses, atherosclerosis, Alzheimer's disease, diabetes, cancer, cardiovascular diseases, and other AGE- and RAGE-related conditions. AGE (advanced glycation end-products) and their receptors, RAGE (receptor for advanced glycation end-products) have been implicated in conditions as diverse as cardiovascular disease and diabetes. AGEs are causative of multiple long term loss of cellular function and eventual disease states, in essence, sugar-protein complexes become chemically cross-linked and degrade normal cellular function, while promoting free radical damage.

The present invention comprises compositions and methods that treat or prevent glycation-related conditions. Compositions of the present invention comprise mineral extract compositions, mogroside/mineral extract compositions, and mogroside compositions as described herein. Methods of the present invention comprise providing an effective amount of a mineral extract composition or a mogroside/mineral extract composition or a mogroside composition to prevent or reduce glycation events occurring in the subject or to treat or prevent glycation-related conditions in humans or animals. Compositions comprising a mineral extract composition or a mogroside/mineral extract composition or a mogroside composition are referred to herein as anti-glycation compositions, but this reference is not intended to limit the activities of the compositions.

Advanced Glycation End-Products (AGEs) have been implicated as critical factors affecting health, wellness, and longevity, particularly in association with inflammation and other disease states. Glycation is the first step in a complex series of non-enzymatic reactions in the body known as Amadori reactions. Schiff base reactions, and Maillard reactions, which lead to AGE formation. A characteristic of certain reactive or precursor AGEs is the formation of covalent crosslinking of proteins, which alters their structure and function, and is found in the cellular matrix, basement membranes, red blood cells, and vessel-wall components. Other major features of AGEs relate to their interaction with, a variety of cell-surface AGE-binding receptors (RAGE), leading to activation and pro-oxidant pro-inflammatory events.

A large body of evidence suggests that AGEs are important pathogenetic mediators of almost all diabetes complications, conventionally grouped into micro- or macroangiopathies. For instance, AGEs are found in retinal vessels of diabetic patients, and their levels correlate with those in serum, as well as with severity of retinopathy. AGEs are now implicated in a vast array of age related degradations from coronary disease to skin aging. Some AGEs are benign, but others are more reactive than the sugars they are derived from, and are implicated in many age-related chronic diseases such as: diabetes mellitus where beta cells are damaged, cardiovascular diseases in which the endothelium, fibrinogen and collagen are damaged, Alzheimer's disease wherein amyloid proteins are side products of the reactions progressing to AGEs, cancer with its release of acrylamide and other side products, peripheral neuropathy and other sensory losses such as deafness due to demyelination, renal dysfunction and blindness which occur because of microvascular damage. This range of diseases shows the extent of the effects of advanced glycation end products interfering with molecular and cellular functioning throughout the body and the other side effects associated with AGE, such as the release of highly-oxidizing side products such as hydrogen peroxide.

Glycated substances are eliminated from the body slowly, and the renal clearance factor is only about 30%. As a consequence, long-lived cells (such as neurons), long-lasting proteins (such as eye crystalline and collagen), and DNA may accumulate substantial damage over time. Metabolically-active cells such as those in kidney's glomeruli, retina cells in the eyes, and beta cells (insulin-producing) in the pancreas are also at high risk of damage. The endothelial cells of the blood vessels are damaged directly by glycation, which has implications in atherosclerosis. Atherosclerotic plaque tends to accumulate at areas of high blood flow due to the increased presentation of sugar molecules, and glycation end-products at these points. Damage by glycation results in stiffening of the collagens in the blood vessel walls, and contributes to high blood pressure. Glycation also causes weakening of blood vessel walls, which may lead to micro- or macro-aneurisms, which in turn, if formed in the brain, may lead to strokes.

In addition to endogenously formed AGE, AGE can also be introduced in the body from exogenous sources. Exogenous AGE may be consumed as "dietary" or "pre-formed" AGE, These are formed when sugars are cooked with proteins or fats. Tobacco smoke, for example, is a well-known exogenous source of AGEs. The combustion of various pre-AGEs in tobacco during smoking gives rise to reactive and toxic AGEs. Serum AGEs or LDL-linked AGEs are significantly elevated in cigarette smokers. Diabetic smokers, as a result, are reported to exhibit greater AGE deposition in their arteries and ocular lenses.

Aminoguanidine, an inhibitor of AGE formation, has been shown to prevent retinopathy in diabetic animals. Also, AGEs accumulate in peripheral nerves of diabetic patients and use of anti-AGE agents improves nerve conduction velocities and corrects neuronal blood flow abnormalities.

Atherosclerosis is significantly accelerated in diabetic patients and is associated with greater risk of cardiovascular and cerebrovascular mortality. Preclinical and clinical studies have shown that AGEs play a significant role in the formation and progression of atherosclerotic lesions. Increased AGE accumulation in the diabetic vascular tissues has been associated with changes in endothelial cell, macrophage, and smooth muscle cell function. In addition, AGEs can modify LDL cholesterol in such a way that it tends to become easily oxidized and deposited within vessel walls, causing streak formation and, in time, atheroma. AGE-crosslink formation results in arterial stiffening with loss of elasticity of large vessels.

AGEs form at a constant but slow rate in the normal body, starting in early embryonic development, and accumulate with time. However, their formation is markedly accelerated with aging or with increased exposure to the sugar sources, such as glucose, fructose and galactose.

It has been surprisingly found that a mineral extract composition or a mogroside/mineral extract composition or a mogroside composition described herein demonstrates anti-glycation properties comparable to or better than aminoguanadine. Minerals are involved in the body in a vast array of complex, reactions, most of which are dependent on mineral chemical characteristics. Minerals and electrolytes maintain fluid and acid-base balance and they are chemically active as cofactors in countless enzyme-catalyzed reactions. The mineral extract compositions or mogroside/mineral extract compositions or mogroside compositions of the present invention may comprise dry powders, liquid formulations, food compositions, cosmetic compositions, and compositions administered by injection. The compositions may be added to a second composition to form a combined composition to provide the anti-glycation activity found in a mineral extract composition or a mogroside/mineral extract composition or a mogroside composition to the second composition.

Compositions of the present invention comprise mineral extract compositions. The method of making such compositions is taught in U.S. Patent Publication No. 2005/0118279. which is herein incorporated in its entirety. Briefly, to make a mineral extract composition of the present invention a soil from a suitable site, comprising the elements as described in U.S. Patent Publication No. 2005/0118279, is collected and subjected to the aqueous extraction process described therein to produce a liquid mineral element composition containing mineral elements which may be dried to produce a dry powder mineral element composition.

Both the liquid mineral extract composition and the dry powder mineral extract composition comprise the mineral elements of a comprehensive mineral composition, as described in U.S. Patent Publication No. 2005/0118279. Both liquid and dry powder mineral extract compositions produced by the procedures described herein generally contain a minimum of 8 macro mineral elements and a minimum of 60 micro mineral elements.

Physical testing and analysis was also conducted on the liquid and dry numeral element compositions;. Typical specifications of the liquid mineral extract composition range in color and may be from yellow to amber brown, and contain, between 1 to 10% by weight of mineral elements, or from 3-5% by weight of mineral elements. The liquid mineral extract composition is acidic with a pH ranging from 2.5-4.5, or from 2.5-3.5. The liquid mineral extract composition can be dried to produce an anhydrous powder. The anhydrous powder may range in color from light- off-while to brown, or from yellow to golden amber, is insoluble in non-polar solvents such as hydrophobic liquids (oil and fats), is insoluble In alcohol, and is readily soluble, yet non-swelling, in water and hydro-alcoholic solutions at concentrations of 1 to 5% by weight, or at concentrations of 3-5% by weight. The dry powder is partially soluble or capable of being partially suspended in polar solvent in supersaturated solutions.

Both liquid and dry mineral extract compositions produced by the procedures described herein may contain a minimum of 8 macro mineral elements and a minimum of 60 micro mineral elements. The micro mineral elements include trace and rare earth mineral elements.

For example the dry mineral ex tract composition may comprise concentration ranging from 0.0001-20.00% by weight percent, from 0.001%-10%, from 0.1% to 20%, from 1% to 20%, from 1% to 10%, from 5% to 10%, from 10-20%, from 10% to 15%, from 15% to 20%, from 1% to 5%, from 5% to 15%, by weight percent, the macro mineral elements of calcium, chlorine, magnesium, manganese, phosphorous, potassium, silicon, and sodium; and, will preferably contain at least sixty micro mineral elements at concentrations ranging from 0.00001-3.0% by weight percent, from 0.0001-1%, from 0.001% to 1%, from 0.01% to 3%, from 0.1% to 3.0%, by weight percent. The micro mineral elements include aluminum, antimony, arsenic, barium, beryllium, bismuth, boron, bromine, cadmium, cerium, cesium, chromium, cobalt, copper, dysprosium, erbium, europium, fluorine, gadolinium, gold, hafnium, holmium, iodine, indium, iridium, iron, lanthanum, lead, lithium, lutetium, mercury, molybdenum, neodymium, nickel, niobium, palladium, platinum, praseodymium, rhenium, rhodium, rubidium, ruthenium, .samarium, scandium, selenium, silver, strontium, sulfur, tantalum, terbium, tellurium, thallium, thorium, thulium, tin, titanium, tungsten, vanadium, ytterbium, yttrium, zinc, and zirconium.

The extraction process used to make the mineral extract compositions of the present invention .normally does not introduce any minerals as part of the extraction process. Therefore, the source materials, the original clay or other soil that is processed through the extraction method, likely include aluminum silicates and other metal silicates in nature that have been naturally enriched with multiple detectable minerals. If a mineral element is identified and quantified in the aqueous liquid extract, generally, it will be identified and quantified in the dry powdered extract in much higher concentrations as a result of drying process or volume reduction.

For example, an extract composition produced using the soil and extractions methods described in U.S. patent application Ser. No. 11/725,729, incorporated herein by reference, was tested by independent analytical testing for conducting chemical analysis using standard techniques of identification and quantification for both dry and liquid forms of the mineral extract composition. The results of testing performed at Teledyne Wah Chang Laboratories in Huntsville, Ala., utilizing scientifically accepted and standard equipment such as titration, inductively coupled plasma, mass spectrometry, and atomic absorption equipment resulted in the mineral element quantification data set forth below in TABLE I for an aqueous mineral extract composition and from the dry mineral extract composition that resulted when the aqueous mineral extract composition was dried to produce a powder.

| Mineral Extract Compostion | | |
|---|---|---|
| Element | Concentration in aqueous liquid composition | Concentration in dry powder |
| Macro Mineral Elements | | |
| Calcium | 2900 ppm | 8% |
| Chlorine | 170 mg/ml | 0.84%* |
| Magnesium | 460 ppm | 0.95% |
| Phosphorous | 0.2 g/L | 0.43% |
| Potassium | 200 mg/L | 1.2% |
| Silicon | 130 mg/L | 0.36% |
| Sodium | 720 mg/L | 2.0% |
| Micro Mineral Elements | | |
| Alunimum | 540 ppm | 0.65% |
| Antimony | 460 ppb | 16.0 ppm |
| Arsenic | 11 ppm | 3.1 ppm |
| Barium | 340 ppb | 11.0 ppm |
| Beryllium | 0.29 ppm | 0.1 ppm |
| Bismuth | <50 ppb | <1.00 ppm |
| Boron | 2.0 mg/L | 72.0 ppm |
| Bromine | *Present as part of Chlorine assay | |
| Cadmium | <50 ppb | 1.10 ppm |
| Total Organic Carbon | 12 g/L | Trace |
| Cerium | 1600 ppb | 68.00 ppm |
| Cesium | 82 ppb | 2.00 ppm |

Mineral Extract Composition (continued)

| Element | Concentration in aqueous liquid composition | Concentration in dry powder |
|---|---|---|
| Chromium | 1.8 ppm | 5.00 ppm |
| Cobalt | 0.25 ppm | 1.00 ppm |
| Copper | 0.09 ppm | <1.00 ppm |
| Dysprosium | 230 ppb | 9.00 ppm |
| Erbium | 150 ppb | 6.00 ppm |
| Europium | <50 ppb | 2.00 ppm |
| Fluorine | *Present as part of Chlorine assay | |
| Gadolinium | 220 ppb | 9.00 ppm |
| Gallium | 70 ppb | 2.40 ppm |
| Germanium | <50 ppb | 1.00 ppm |
| Gold | <50 ppm | 1.00 ppm |
| Hafnium | <0.5 mg/L | 5.00 ppm |
| Holmium | <50 ppb | 2.00 ppm |
| Iodine | *Present as part of Chlorine assay | |
| Indium | <50 ppb | Trace |
| Iron | 730 ppm | 28.00 ppm |
| Lanthamum | 650 ppb | 28.00 ppm |
| Lead | <50 ppb | <1.00 ppm |
| Lithium | 0.9 mg/L | <1.00 ppm |
| Lutetium | <50 ppb | <1.00 ppm |
| Mercury | Trace | <1.00 ppm |
| Molybdenum | 3200 ppb | 120.00 ppm |
| Neodymium | 1000 ppb | 45.00 ppm |
| Nickel | 0.74 ppm | 2.00 ppm |
| Niobium | 96 ppb | 3.00 ppm |
| Palladium | <500 ppb | <1.00 ppm |
| Platinum | <50 ppb | <1.00 ppm |
| Praseodymium | 290 ppb | 10.00 ppm |
| Rhenium | <50 ppb | <1.00 ppm |
| Rhodium | <50 ppb | <1.00 ppm |
| Rubidium | 360 ppb | 11.00 ppm |
| Ruthenium | <50 ppb | <1.00 ppm |
| Samarium | 250 ppb | 10.00 ppm |
| Scandium | <400 ppb | 4.00 ppm |
| Selenium | 0.63 mg/L | 21.00 ppm |
| Silver | <0.02 ppm | <5.00 ppm |
| Strontium | 14000 ppb | 420.00 ppm |
| Sulfur | 1.1 g/L | 1.8% |
| Tantalum | <50 ppb | <1.00 ppm |
| Terbium | <50 ppb | 2.00 ppm |
| Tellurium | <50 ppb | <1.00 ppm |
| Thallium | <50 ppb | 1.00 ppm |
| Thorium | 640 ppm | 22.00 ppm |
| Thulium | <50 ppb | 1.00 ppm |
| Tin | <50 ppb | <1.00 ppm |
| Titanium | 9.34 ppm | 210.00 ppm |
| Tungsten | 52 ppb | 17.00 ppm |
| Vanadium | 4.3 ppm | 14.00 ppm |
| Ytterbium | 140 ppb | 6.00 ppm |
| Yttrium | 1300 ppb | 61.00 ppm |
| Zinc | 1.2 ppm | 14.00 ppm |
| Zirconium | 2.0 mg/L | 62.00 ppm |

The mineral extract compositions set forth above in Table I were produced from naturally occurring soil the analysis of which is reflected below in Table II.

TABLE II

Analysis of Naturally Occurring Soil
Macro Mineral Elements

| Element | Concentration in ppm by weight unless noted as % (for weight percent) |
|---|---|
| Silicon | 25.0% |
| Aluminum | 9.3% |
| Potassium | 4.8% |
| Magnesium | 0.83% |
| Sulfur | 1.6% |
| Iron | 1.6% |
| Calcium | 4.1% |
| Titanium | 0.23% |
| Sodium | 0.138% |
| Manganese | 150 |
| Gallium | 25 |
| Molybdenum | 61 |
| Germanium | 25 |
| Iodine | 7 |
| Bromine | 5.2 |
| Tungsten | 8.1 |
| Hafnium | 2.0 |
| Tantalum | 0.50 |
| Zirconium | 10 |
| Arsenic | 0.2 |
| Antimony | 29 |
| Selenium | 4.1 |
| Zinc | 20 |
| Samarium | 3.5 |
| Holmium | 1.1 |
| Terbium | .62 |
| Iridium | .51 |
| Lutetium | .45 |
| Chromium | 70 |
| Lanthanum | 15 |
| Ruthenium | 7.8 |
| Yttrium | 1.2 |
| Indium | .38 |
| Lead (under) | 17 |
| Niobium | 2.89 |
| Carbon | .19 |
| Hydrogen | .05 |
| Nitrogen | .03 |
| Scandium | 3.7 |
| Cobalt | 4.8 |
| Ytterbium | 1.4 |
| Strontium | 240 |
| Barium | 390 |
| Gold | .68 |
| Europium | .49 |
| Neodymium | 20 |
| Cerium | 40 |
| Cesium | 183 |
| Thorium | Above 100 |
| Uranium | Above 100 |
| Nickel | 60 |
| Beryllium | .10 |
| Bismuth | 14.3 |
| Boron | 7 |
| Cadmium | 1.12 |
| Chloride | 6100 |
| Copper | 2.2 |
| Fluoride | 3.85 |
| Lithium | 1.44 |
| Mercury | 0.166 |
| Palladium | 0.74 |
| Phosphate | 320 |
| Platinum | 0.08 |
| Rhodium | 0.44 |
| Rubidium | 36.5 |
| Silver | 0.3 |
| Tellurium | 0.1 |
| Thulium | 0.65 |
| Tin | 0.44 |
| Vanadium | 8 |
| Dysprosium | 4.0 |
| Praseodymium | 2.0 |
| Thallium | 10 |
| Rhenium | 1.0 |
| Erbium | 2.0 |
| Oxygen | 0.2 |

Once a desirable naturally occurring soil or soil combination is obtained, the soil(s) is subjected to the extraction process described by U.S. patent application Ser. No. 11/725, 729. Clay soils, mixtures of clay soils, or mixtures of clay soil(s) and leonardite are preferred in the practice of the invention. One reason such soil combinations are preferred is that such soils can be high in the mineral elements deemed important in the practice of the invention. As noted, it is preferred that mineral extract compositions produced in accordance with the invention include at least eight macro mineral elements and at least sixty micro mineral elements.

The first step in determining whether a clay soil is acceptable as a source material is to determine of arsenic, lead, mercury, and cadmium are each present in acceptably small concentrations. An aspect of the present invention comprises compositions having the concentration of each of these elements in lower amounts than the concentrations shown below in Table III.

TABLE III

Maximum Desired Concentrations of Toxic Elements

| Element | Maximum Desired Soil Concentration in ppm or ppb |
|---|---|
| Arsenic | 0.2 ppm |
| Lead | 0.17 ppb |
| Mercury | 0.116 ppm |
| Cadmium | 1.12 ppm |

TABLE IV

Preferred Minimum Concentrations of Selected Rare Earth Elements in Naturally Occurring Soil

| Element | Preferred Minimum Soil Conc |
|---|---|
| Cerium | 40 |
| Praseodymium | 2 |
| Neodymium | 20 |
| Samarium | 3.5 |
| Europium | 0.49 |
| Terbium | 0.62 |
| Dysprosium | 4 |
| Holmium | 1 |
| Erbium | 2 |
| Thulium | 0.65 |
| Ytterbium | 1.2 |
| Lutetium | 0.45 |

The concentration of the elements listed in Table IV can vary as desired, but, as noted, it is desirable to have at least the concentration of each element as noted in Table IV. Source material soil for composition of the present invention may or may not comprise one or all of the rare earth elements listed in Table IV. For example, a lanthanum concentration of at least, eighteen ppm and a scandium concentration of at least three and seven-tenths ppm may be found in a source material soil. Concentrations, of promethium and gadolinium may also be found. Source material soil for composition of the present invention may or may not comprise at least ten rare earth elements, at least twelve, or more rare earth elements and optionally include lanthanum and scandium. Though not wishing to be bound by any particular theory, it Is theorized that the presence of rare earth elements in the soil, and in the mineral extract compositions derived from the source material soil, is believed to be useful in improving the efficacy of the mineral extract compositions when ingested or when transdermally absorbed by the body.

Once a clay soil or clay and soil combination is provided or is combined to yield the mineral elements, as taught by U.S. patent application Ser. No. 11/725,729, the source material soil is subjected to the extraction process as taught by U.S. patent application Ser. No. 11/725,739, to yield the mineral extract compositions comprised in the anti-glycation compositions of the present invention.

In general, the extraction of the source material soil uses the following steps. Water, typically purified using known methods such as reverse osmosis, is added to citric acid and the source material soil in a mixing tank. The amount of citric acid (or of phosphoric acid or other edible acid(s)) or combinations thereof, may be in the range of 0.25% to 7.5% of the weight, of water utilized, but typically is in the range of 1.0% to 2.0%. The water, citric acid and source material soil, form a slurry and is gently agitated (for example, with a blade slowly rotating at from one to ten RPM) for about an hour, although the agitation time can vary as desired. The slurry from the tank is directed into a settling tank to permit particulates to settle downwardly out of the slurry. The slurry is maintained in the settling tank for any desired length of time, in the range of about one to ten days. As the length of time that the slurry is maintained in the settling tank increases, the amount of liquid that can be drawn out of the tank and sent to a cooling tank or concentrator increases and the amount of solids that have settled to the bottom of the tank increases. Additives can be used to facilitate the settling of solids from slurry. After the slurry has resided in settling tank for the desired period of time, liquid is drawn out of the tank to a cooling tank, or directly to the concentrator. The solids on the bottom of tank can be reprocessed, discarded, or can be otherwise utilized.

The cooling tank cools the fluid from the settling tank to a temperature in the range of 40-70° F. (5 to 21° C.). Cooled liquid is sent to the concentrator.

The concentrator removes water from the cooled liquid. This may be accomplished using known methods such as a thin film composite reverse osmosis system or evaporation. The resulting concentrate liquid, comprising the minerals extracted from the original slurry, is directed to a cooling tank or to a dryer, depending if storage or further processing is desired. The cooling rank cools the concentrate liquid to 40 to 70° F. (5 to 20° C.) to prevent the growth and yeast and mold.

The concentrate liquid produced by concentrator has a pH of approximately 3. The concentrate liquid typically includes from three to twelve percent by weight mineral elements, i.e. if the mineral elements are separated from the concentrate liquid, a dry material is produced that has a weight equaling about 3% to 12% by weight of the concentrate liquid. The pH of the concentrate liquid is adjusted by varying the amount of citric acid or other edible acid and/or alkaline or acidic soil added to the mixing tank and is in the range of pH 2.0 to pH 5.0, preferably pH 2.5 to pH 3.5. The pH of the concentrate liquid (and dry powder or Other material produced therefrom) preferably is less than pH 4.5. A mineral extract concentration of at least eight percent may be provided for injection into a dryer. Any desired drying system can be utilized, such as a tower into which the concentrate liquid is sprayed to produce a powder.

Anti-glycation compositions of the present invention may comprise a mineral extract composition, such as that, shown in Table I, or a mogroside/mineral extract composition or a mogroside composition, combined or admixed with a second component. A mineral extract composition has activity for energy production, and collagen growth stimulation. Other activities of a mineral extract composition may be found in U.S. patent application Ser. Nos. 10/725,729, 11/472,536 and 11/638,311, each of which is herein incorporated in its entirety. A second component of the anti-glycation compositions may be a liquid or a dry component, to form liquid or dry compositions. Liquid anti-glycation compositions comprise a mineral extract composition, a mogroside/mineral extract composition or a mogroside composition, in either a dry powder form or a liquid form, and a liquid, including but not limited to, water, which may be still or carbonated, and other ready to drink or ready to mix beverages, including but not limited to coffees, teas, energy drinks, juices, milks, and plant liquids such as soy products, sugar cane products, coconut products, protein drinks, meal replacement drinks, and alcohol containing products such as beer and wine. Liquid anti-glycation compositions may comprise pharmaceutical nutraceutical or dietary supplement compositions in combination with a mineral extract composition. For example, an anti-glycation composition may comprise liquid pharmaceutically acceptable syrups, excipients, fillers or other known pharmaceutical formulations in combination with a mineral extract composition, a mogroside/mineral extract composition or a mogroside composition. As a further example, an anti-glycation composition may comprise a mineral extract composition, a mogroside/mineral extract composition or a mogroside composition in a pharmaceutical formulation for ocular drops to provide anti-glycation effects to the eye, for example for diabetics, to treat vision impairment.

Solid or dry anti-glycation compositions comprise a mineral extract composition or a mogroside/mineral extract composition or a mogroside composition, and a solid or dry material, such as a food product for ingestion by a human or animal. Solids or dry materials include, but are not limited to, foodstuffs, food products, nutritive and non nutritive sweeteners, pharmaceutical, nutraceutical or dietary supplement formulations. For example, an anti-glycation composition may comprise solid or dry pharmaceutically acceptable compositions, excipients, fillers or other known pharmaceutical formulations, to be made into dosage units such as tablets, capsules or powders, in combination with a mineral extract composition, a mogroside/mineral extract composition or a mogroside composition. The compositions of the present invention may function as additives to foods, and be combined with food products, including foods wherein a dry or liquid a mineral extract composition, a mogroside/mineral extract composition or a mogroside composition can be added, so as to provide anti-glycation activity to the food.

As a specific example, an anti-glycation composition may be added to a food product for human or animal consumption. An anti-glycation sweetener may comprise a mineral extract composition, a mogroside/mineral extract composition or a mogroside composition alone, or in combination with a compound or composition that has a sweet taste, or is a recognized sweetening agent. Anti-glycation compositions may be used as a sweetening agent, and may comprise a mineral extract composition combined with sweeteners, including but not limited to sweet natural compounds or compositions such sucrose or maple syrup, or artificial sweeteners. The anti-glycation mineral extract composition may be combined with a sweetener, comprising mogroside, to form a mogroside/mineral extract composition, an anti-glycation sweetener. A mineral extract composition may be added to a sweetener compound or composition, and used for example as a coating in a continuous spray agglomeration to sugar granules, or added to an alternative natural sweetener such as erythritol, to provide the sweetener with anti-glycation properties. The mineral extract composition may be added as a liquid to a stevia extract to provide a combined stevia/mineral extract composition sweetener with anti-glycation properties. A mineral extract composition, a mogroside/mineral extract composition or a mogroside composition may be added to sweeteners known to promote AGE such as high fructose corn syrup to provide an anti-glycation a mineral extract, composition, a mogroside/mineral extract composition or a mogroside composition high fructose corn syrup composition.

Anti-glycation activity, or glycation inhibition activity, are terms which are used interchangeably, and refer to the ability of a compound, extract, or composition to interfere with glycation reactions such that the reaction of amino groups of proteins, lipids, or nucleic acids with sugar aldehyde or keto groups to produce modified amino groups, are altered or prevented or the formation of advanced glycosylation end-products (AGE) are altered or prevented, in vivo or in vitro.

A composition of the present invention comprises natural sweetener compounds, including but not limited to those derived from Luo Han Guo, which may be used as an anti-glycation sweetener alone or with other components of a composition such as a mineral extract composition taught herein. Luo Han Guo is a botanical plant also known as Momordica Grosvenori or Siraitia grosverorii, originally grown in China and now grown there and in other places where climate permits. Usually sweetener compounds, such as those known as mogrosides, are derived from the fruit of the Luo Han Guo plant, though any portion of the plant may be processed to yield sweetener compounds, Luo Han Guo fruit is a small gourd-like fruit having an intensely sweet taste. The fruit contains a naturally occurring compounds called mogrosides, which is thought to be three hundred times sweeter than cane sugar and is low in calories. Herein, the term mogroside is used to mean one or more, or all of the mogroside compounds present in Luo Han Guo fruit, and mogroside is also referred to as Lou Han Guo extract. In literature, the Luo Han Guo plant is also referred to as Lo Han Guo or luohan guo, all of which are intended to refer to the same plant.

Surprisingly, the inventors have found that mogroside has anti-glycation activity, along with energy promotion and collagen growth stimulation. Methods of the present invention comprise use of a mogroside composition for anti-glycation activity, energy promotion and collagen stimulation in compositions for sweetening foods or drinks. Mogroside compositions in combination with mineral extract compositions such as those taught herein, are referred to herein as mogroside/mineral extract compositions. Mogroside compositions comprise a mogroside extract from Luo Han Guo fruit, and methods for making mogroside or a Luo Man Guo fruit extract are known.

An effective amount of a mineral extract composition or a mogroside/mineral extract composition or a mogroside composition for anti-glycation activity may or may not be dependent on the type of second component to which a mineral extract composition or a mogroside/mineral extract composition or a mogroside composition is added. An anti-glycation composition may be provided or administered to a subject 1 time a day, two times a day, three times a day or more often. An anti-glycation composition may be administered daily, weekly, or monthly in a regular schedule or on an as needed schedule. In general an anti-glycation composition may comprise from about 0.0001 g to about 1000 g of the mineral extract, or from about 0.0001 g to about 100 g, from about 0.0001 g to about 10 g, from about 0.001 g to about 1000 g, from about 0.01 g to about 1000 g, from about 0.1 g to about 1000 g, from about 1.0 g to about 100 g, from about 1.0 g to about 10 g, from about 10 g to about 1000 g, and ranges therein between. For example, a 12 oz enhanced water beverage may contain 0.1 gram of a mineral extract composition, while a 10 oz carbonated beverage with high fructose corn syrup may contain 10 grams of a mineral extract composition, and a gallon size maple syrup may contain 300 grams of a mineral extract composition.

A mogroside/mineral extract composition may comprise about 0.0001 g to about 1000 g of the mineral extract; as described above, which is added to a mogroside composition comprising mogroside in amounts of about 0.0001 g to about 1000 g.

A mineral extract composition resulting from the selection of source material soils and the extraction process are comprised in the anti-glycation compositions that are used in the methods of the present invention. Methods of the present invention include methods of inhibiting formation of glycation end products, inhibition of AGE formation, inhibition of glycation reactions of proteins, lipids and/or nucleic acids, inhibition of aging effects related to glycation reaction, and methods for treatment or prevention of glycation-related conditions including, but not limited to, complications of diabetes (Type I and II), rheumatoid arthritis, Alzheimer's disease, uremia, neurotoxicity, atherosclerosis, inflammatory reactions, ventricular hypertrophy, angiopathy, myocarditis, nephritis, arthritis, glomerulonephritis, microangiopathies, and renal insufficiency, or methods of preventing accumulation of glycation products. Methods for inhibiting glycation or inhibiting AGE formation, prevention or treatment of glycation-related conditions comprise administering or providing an effective amount of an anti-glycation composition comprising a mineral extract composition or a mogroside/mineral extract composition or a mogroside composition, to a human or animal, wherein the anti-glycation composition alters the effects of glycation, glycation activity, glycation rate or amount of glycation products such as AGE in the subject. For example, an amount of glycation activity can be conveniently measured by an A1C test of glycated hemoglobin. A reduction in the A1C measurement indicates a lower amount of glycation activity in the body. Measurements for glycated proteins are known to those skilled in the art, see for example U.S. Pat. No. 5,506,144.

Methods of the present invention, comprise making and using anti-glycation compositions. Such compositions may be consumed by healthy young and adult animals and humans, as well as humans or animals at risk for developing, or suffering from, diabetes, atherosclerosis or similar glycation-related conditions. Food, beverages, and nutritional supplement anti-glycation compositions may be used to provide anti-glycation potential to a subject and provide a benefit in lowering the potential cross-linking of protein and sugars to promote health and wellness. For example, a line of food or beverages having anti-glycation capability due to the incorporation of a mineral extract composition of the present invention may be used by different ages for multiple health benefits.

Methods of treatment or prevention of glycation-related conditions or inhibition of glycation levels include providing an effective amount of an anti-glycation composition comprising a mineral extract composition, or a mogroside/mineral extract composition or a mogroside composition for intestinal inflammation. Intestinal inflammation may affect the immune and nervous systems and contribute to a variety of conditions including food intolerances, allergic reactions, inflammation, cognitive difficulties, hyperactivity and other behavioral issues. Receptor for Advanced Glycation End-products (RAGE) is a family of cell surface receptors associated with inflammatory responses. It is currently believed that RAGE are involved in inflammatory responses in the intestines when consumption of glycation promoting products contact the intestinal and stomach epithelial cell lining. It has been shown that RAGE are expressed in intestinal epithelial cells, primarily concentrated at the lateral membranes close to the apical cell junction complexes. Although RAGE expression is low in epithelium under normal conditions, it is up-regulated during consumption of sugars. The glycation effect that takes place when eating sugars leads to crosslinking and inflammation of the intestinal and stomach walls.

In the methods of the present invention for prevention or treatment of glycation-related conditions, or inhibition of glycation products and AGE, for example, a beverage or foodstuff comprising an anti-glycation composition such as a mineral extract composition or a mogroside/mineral extract composition or a mogroside composition may be ingested by subjects, animals or humans, to reduce the effects of glycation on the linings of the gastrointestinal system. Such anti-glycation compositions may support intestinal anti-glycation effects, enhance intestinal detoxification of oxidative compounds, promote intestinal nutrient absorption help retard intestinal inflammatory processes, promote the intestinal role as a gatekeeper of AGEs to the circulatory pathway, encourage intestinal health and help reduce the factors of inflammation, and aid in calming and soothing intestinal glycation-induced inflammation. Beverages or foodstuff, in addition to comprising an anti-glycation composition, may also comprise botanicals such as chamomile, dandelion, echinecea, milk thistle, gentian, licorice, chickenweed, meadowsweet, goldenseal, spanish black radish, and chlorophyll.

Methods of prevention or treatment of glycation-related conditions, or inhibition of glycation products and AGE, include providing an effective amount of an anti-glycation composition comprising a mineral extract composition or a mogroside/mineral extract composition or a mogroside composition for cognitive function. Cognition is a general term covering many aspects of brain function, including learning, remembering, thinking and reasoning. These processes may decline during the natural aging process or in the event of degenerative disease. Advanced glycation end products and free radical damage may be a natural part of aging, leading to reduced cognitive function and motor skills, and may lead to accelerated forms of dementia, Alzheimer's or Parkinson's disease. For example, a beverage or foodstuff comprising an anti-glycation composition may be ingested by subjects, animals or humans, to reduce the effects of glycation on the nervous system, reduce inflammatory reactions, and prevent damage to the circulatory system. Such anti-glycation compositions may be used to protect against cognitive degradation, restore optimal cognitive functionality, encourage healthy cognitive function, enhance cognitive performance, promote healthy brain function, aid in combating oxidative-induced cognitive degradation, strengthen cognitive function defense, and to stimulate coherent cognitive processes. Beverages or foodstuff, in addition to comprising an anti-glycation composition, may also comprise herbal or botanical compounds or extracts of ginko biloba, ginseng, vipocetine, green tea, soy isoflavones, Vitamins E, C, B6, B12, phospholipids (phosphatidylserine and phosphatidylcholine) and citocoline (a precursor) and glycerophosphocholine, alpha lipoic acid, acetyl-L-carnitine, coenzyme Q 10, creatine, essential fatty acids, DNA, EPA, and resveratrol, or grapeseed extract.

Methods of prevention or treatment of glycation-related conditions, or inhibition of glycation products and AGE, include providing an effective amount of an anti-glycation composition comprising a mineral extract composition or a mogroside/mineral extract composition or a mogroside composition for vision. A major risk factor in vision loss, cataracts, and macular degeneration is the hardening of the arteries, capillaries and retina in the eyes. It is well established that diabetics suffer a much higher incidence of vision impairment relative to the general population, in part as a result of advanced glycation end product accumulation in the eye. For example, a beverage or foodstuff comprising an anti-glycation composition may be ingested by subjects, animals or humans, to reduce the effects of glycation on the eye and associated structures. Such compositions are useful for promoting vision wellness, defending against age related vision degradation, restoring eye capillary circulation, protecting against age related vision impairment, protecting against glycation-induced vision impairment, reducing age related vision impairment, promoting health of the eyes, encouraging lens clarity, and sustaining healthy vision. Beverages or foodstuffs, in addition to comprising an anti-glycation composition, may also comprise herbals such as bilberry, ginkgo biloba, phytonutrients such as lutein, zeaxanthin, lycopene, bioflavonoids, mixed carotenoids, lipoic acid, n-acetylcysteine, and quercetin, amino acids such as taurine, glutathione, cysteine, vitamins, such as Vitamin A, C, E, B-12, betacarotene, essential fatty acids, and other antioxidants (i.e. melatonin)

Methods of prevention or treatment of glycation-related conditions, or inhibition of glycation produces and AGE include providing an effective amount of an anti-glycation composition comprising a mineral extract composition or mogroside/mineral extract composition or mogroside composition for arthritis. Advanced glycation end products (AGEs) are thought to be promoters of inflammation and eventual joint degradation as seen in osteoarthritis and rheumatoid arthritis. It has been shown that AGEs activate inflammation mediators called MMPs to begin the cascading effect of pain and limited movement flexibility. Synovial fluids become oxidized and subject to glycation-driven hardening. Markers of glycation have been identified as present in elevated amounts in synovial fluids of osteoarthritis and rheumatoid arthritis patients indicating glycation is a factor in these conditions. Prophylactic use of anti-glycation compositions of the present invention at an early age may prevent or delay the onset of these conditions and, intake at any age may reduce the incidence and severity of osteoarthritis and rheumatoid arthritis. Taken at any age, the anti-glycation compositions of the present invention may limit the cascading damage of glycation and thus reduce the propensity to promote longer term arthritic diseases that come with aging.

For example, a beverage or a foodstuff or food product comprising an anti-glycation composition may be ingested by subjects, animals or humans, to reduce the effects of glycation on the joints or synovial fluid. Such compositions may be used to retard age-related arthritic degeneration, maintain joint and tendon flexibility, promote healthy bone strength and joint elasticity, encourage bone structure integrity and flexibility, defend against glycation-induced joint degradation, promote healthy synovial environment to joints and tendons, encourage more active lifestyle when living with arthritis, promote longer preventive wellness for arthritis, and reduce incidence of inflammation, point swelling and tightness.

Beverages or foodstuff in addition to comprising an anti-glycation composition, may also comprise herbals or extracts of herbals such as ginger, chinese thunder god vine, willow bark extract, feverfew, cat's claw, stinging nettle, boswellia, S-adenosylmethionine (SAMe), chondroitin sulfate, glucosamine, essential fatty acids, and enzymes, such as bromelain, and quercetin.

Methods of prevention or treatment of glycation-related conditions, or inhibition of glycation products and AGE include providing an effective amount of an anti-glycation composition comprising a mineral extract composition or a mogroside/mineral extract composition or a mogroside composition for erectile dysfunction (ED). Glycation has been proposed to play a role in age-related processes by forming protein and DNA adducts and cross-links. These cross-links may contribute to erectile dysfunction by scavenging nitric oxide, which is needed for erection. Additionally, glycation causes hardening of arteries which inhibits the arterial flexibility required to maintain an erection. AGE have been demonstrated to impair erectile function by affecting the functional capabilities of the corpus cavernosum and by interfering with the production of natural penile vasodilating agents, endothelial and neuronal nitric oxide (NO). For example, a beverage or foodstuff comprising an anti-glycation composition may be ingested by subjects, animals or humans, to reduce the effects of glycation on the ability to acquire and maintain an erection. Such competitions may be used to promote healthy sexual function, retard age related ED circulatory degradation, prevent glycation-induced ED, to maximize sexual circulation processes, enhance healthy erectile performance, and encourage normal erectile performance. Beverages or foodstuff, in addition to comprising an anti-glycation composition, may also comprise Vitamin C & E, bioflavonoids, essential fatty acids, yohimbe bark, horny goat weed, maca, saw palmetto, and man bao.

Anti-glycation compositions for these and other glycation-related conditions may comprise ready-to-eat-cereals, fruit juices, candy bars, chewing gum, nutritional supplements, enhanced water beverages, carbonated and non-carbonated drinks, alcoholic beverages such as beer and wine, baby food, and many other foodstuffs and beverages. The anti-glycation compositions of the present invention may be used an animal feed additive.

AGEs are thought to play a role in decreasing cellular metabolic rate and function. The anti-glycation mineral extract composition of the present invention may play a rote in retarding the decrease in metabolic rate due to glycation endproducts. In addition, the anti-glycation compositions of the present invention may also provide energy to the ceils of the body by enhancing mitochondrial function. See examples herein where the compositions taught herein are effective in mitochondrial metabolism. For example, a beverage or foodstuff comprising an anti-glycation composition comprising the mineral extract composition or a mogroside/mineral extract composition or a mogroside composition may be ingested by subjects, animals or humans, to enhance energy metabolism in the body. Such compositions provide chemical stimulant-free metabolic enhancement.

AGEs are thought to play a role in degrading collagen. The anti-glycation compositions of the present invention may play a role in retarding collagen degradation due to glycation endproducte. Methods of prevention or treatment of glycation-related conditions, or inhibition of glycation products and AGE include providing an effective amount of an anti-glycation composition comprising a mineral extract composition or a mogroside/mineral extract composition or a mogroside composition for collagen production and maintenance. Collagen is a family of highly characteristic, fibrous proteins constituting 25 percent of total protein mass in human body. With aging, collagen production decreases and collagen degeneration increase. Whether to promote younger skin, for healthier bones and tendons, collagen stimulation is a desirable attribute for an ingredient in food and beverages. Examples of stimulation of type I collagen to nearly 90% above the non-treated (water) control is shown herein. MMPs, matrix metalloproteinases, are proteolytic enzymes or proteases that digest or breakdown proteins in the body. Over 30 different types of MMPs have been discovered to date for multiple enzymatic digestive functions and inflammation mediation. On skin, the primary role of MMP enzymes is to maintain, a steady state of recycling the skin matrix, particularly the structural proteins collagen and some are part of the inflammation pathway. As part of aging, MMPs tend to over-express themselves. In addition, inflammation, irritation, and environmental stress (free radicals) elevate the levels of MMP in the skin to create greater digestion of collagen. In vitro studies taught herein using human fibroblast indicate a mineral extract composition of the present invention efficiently blocks collagen-digesting enzymes at concentrations levels as low as 0.005%. At concentration levels of 0.05%, a 100% inhibitory effect on MMP was seen.

AGEs are oxidative promoters of free radicals. Anti-glycation compositions of the present invention may play a role in combating free radicals that are generated by glycation endproducts. Methods of the present invention comprise treatment or inhibition of oxidation comprising providing an effective amount of an antioxidant composition comprising a mineral extract composition or a mogroside/mineral extract composition or a mogroside composition described herein in combination with a second component such as a foodstuff or beverage. There are many environmental and lifestyle factors which increase the level of oxidation in living cells to unhealthy levels, all which accelerate the aging process and create potential for disease. Because of its damaging effect on vital biological systems, oxidative stress has been implicated in more than 100 diseases and in aging. Antioxidants are intimately involved in the prevention of cellular damage—the common pathway for cancer, aging, and a variety of other diseases. Endurance exercises can increase oxygen utilization from 10 to 20 times over the resting state. This greatly increases the generation of tree radicals, prompting concern about enhanced damage to muscles and other tissues. Beverages or foodstuff, in addition to comprising an antioxidant composition comprising a mineral extract composition or a mogroside/mineral extract composition or a mogroside composition of the present invention, may also comprise vitamins A, C and E, and plant polyphenols.

Though not wishing to be bound by any particular theory, it is currently believed that skin aging is accelerated by AGEs and their effects on degradation of HA and collagen, free radicals and inflammation. The mineral extract compositions or mogroside/mineral extract compositions or mogroside compositions disclosed herein may increase the concentrations of hyaluronic acid (HA) as demonstrated in the following example. This could additionally aid in the synovial fluid environment. Ability to increase HA was assessed with adult human dermal fibroblasts plated in high glucose DMEM supplemented with 5% serum at 10,000 cells per well and a mineral extract composition was added. After 5 days, cell culture conditioned media were collected and samples of 100 ul per test condition were used in the HA assay. HA assay was performed using Hyaluronan Enzyme-Linked Immunosorbent Assay Kit (HA-ELISA, cat. #K-1200) from Echelon (Salt Lake City, Utah). The mineral extract composition was observed to produce >20% HA stimulation. Coupled with the anti-glycation, collagen stimulation and protection. anti-inflammatory and antioxidant properties, methods of prevention or treatment of glycation-related conditions, or inhibition of glycation products and AGE, include providing an effective amount of an anti-glycation composition comprising a mineral extract composition or a mogroside/mineral extract composition or a mogroside composition for topical cosmetic treatments or orally administered beautification products, such as beverages and foodstuff for treatment of skin anti-aging. Since, advanced glycation end products (AGEs) have been established as promoters of inflammation, inflammation has been established as a promoter of skin aging.

In general, the present invention comprises anti-glycation compositions and methods of making and using anti-glycation compositions, and methods for treating and preventing glycation-related conditions. A method of treating or preventing glycation-related conditions, comprises administering to a human or animal an effective amount of an anti-glycation composition comprising a mineral extract composition or a mogroside/mineral extract composition or a mogroside composition, wherein the amount is effective in reducing at least a portion of the glycation events in a human or animal. An anti-glycation composition may comprise a mineral extract composition, an anti-glycation composition may comprise a mogroside/mineral extract composition, or an anti-glycation composition may comprise a mogroside composition. An anti-glycation composition may further comprise a foodstuff or a beverage. Glycation-related conditions comprise formation of glycation end products, AGE formation, glycation reactions of proteins, lipids and/or nucleic acids, aging effects related to glycation reactions, and complications of diabetes (Type I and II), rheumatoid arthritis, Alzheimer's disease, uremia, neurotoxicity, atherosclerosis, inflammatory reactions, ventricular hypertrophy, angiopathy, myocarditis, nephritis, arthritis, glomerulonephritis, microangiopathies, and renal insufficiency, or accumulation of glycation products.

An anti-glycation composition may comprise a mogroside and a mineral extract composition in combination, and may be farther combined with a foodstuff or a beverage. An anti-glycation composition may comprise a mogroside and a mineral extract composition in combination, and may be further combined with a sweetener composition.

A method of inhibiting glycation reactions comprises providing an effective amount of an anti-glycation composition comprising a mineral extract composition or a mogroside/mineral extract composition or a mogroside composition, and inhibiting a glycation reaction. The method may comprise an anti-glycation composition comprising a mineral extract composition, an anti-glycation composition comprising a mogroside/mineral extract composition, or an anti-glycation composition comprising a mogroside composition. The method may further comprise an anti-glycation composition comprising a foodstuff or a beverage. The method may comprise providing an anti-glycation composition in vivo to a human or animal or may be provided in vitro.

Definitions Used Herein

Chemical element. Any of more than 100 fundamental metallic and nonmetallic substances that consist of atoms of only one kind and that either singly or in combination constitute all matter, most of these substances lighter in weight than and including uranium being found in nature and the rest being produced artificially by causing changes in the atom nucleus.

Clay. A natural or synthetic colloidal lusterless earthy composition that includes tiny sheet-like layered particles of alumina and/or silica that are less than about 0.002 millimeters in size, that is generally plastic when moist, and that, when naturally occurring, includes decomposed igneous and/or metamorphic rocks. Most clays have a pH in the range of about 4.5 to 8.5. Natural and synthetic clays include mineral elements. Clays can, in additional to having particles less than five microns in size, include particles having a size greater than five microns.

Leonardite. A soft, loose-textured coal that has low BTU value. Leonardite is a humate, can include up to 70% by weight minerals, can be formed from lignite, can occur naturally as die result of not being heated and pressurized over time to the extent necessary to produce anthracite, lignite, or bituminous coal, and, can include compost as a component.

Mineral. Any naturally occurring chemical element or compound. A mineral has a characteristic crystal structure and chemical composition or range of compositions.

Mineral element. A chemical element that occurs naturally as or in a mineral. A mineral element may be produced using synthetic, or manufacturing processes, however, each mineral element does occur naturally as or in a mineral.

Rare earth or rare earth element. Any one of a group of metallic elements with atomic numbers 58 through 71, including cerium, praseodymium, neodymium, promethium, samarium, euro0pium, gadolinium, terbium, dysprosium, holmium, erbium, thulium, ytterbium, and lutetium. In nature, rare earth elements are bound in combination with nonmetallic elements m the form of phosphates, carbonates, fluorides, silicates, and tantalates.

Sand. A loose material consisting of small bat easily distinguishable grains usually less than two millimeters in diameter and more than about 0.02 millimeters in diameter, most commonly of quartz, resulting from the disintegration of rocks.

Silt. Unconsolidated or loose sedimentary material whose constituent rock particles are finer than grains of sand and larger than clay particles, specifically, material consisting of mineral soil particles ranging in diameter from about 0.02 to 0.002 millimeters.

It must be noted that as used in this specification and the appended claims, the singular forms "a," "an," and "the" include plural referents unless the context dearly dictates otherwise.

All patents, patent applications and references included herein are specifically incorporated by reference in their entireties.

It should be understood, of course, that the foregoing relates only to preferred embodiments of the present invention and that numerous modifications or alterations may be made therein without departing from the spirit and the scope of the invention as set forth in this disclosure.

The present invention is further illustrated by the following examples, which are not to be construed its any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Example 1

Three mineral extract compositions were evaluated to test the anti-glycation effect.

Each reaction mixture contained 10 mg/ml albumin (Sigma) in PBS with 500 mM glucose (Sigma G8270) in PBS. The negative control was 10 mg/ml albumin without glucose. A negative control was used for each experimental point. The positive control was 10 mg/ml albumin with 500 mM glucose with 1 mM aminoguanidine hydrochloride (Sigma 396494).

Sample Preparation

Each mineral extract composition was diluted in type I sterile water to 10 mg/ml, sterilized by 0.22 micron filtration and incubated at dilutions 100 ug/ml, 10 ug/ml, 1 ug/ml and 0.1 ug/ml with the reaction mixture with or without glucose for 11 days at 37° C. in the presence of sodium azide.

Protein glycation was detected by the increase of non-tryptophan fluorescence (excitation at 360 nm, emission at 460 nm) using microplate fluorometer Cytofluor 2350 (Millipore), as described (Argirova and Argirov, 2003). The glycation value for each experimental point was obtained by subtracting the background reading (samples without glucose).

Results and Discussion

As seen in FIG. 1, 0 is the negative control, and each mineral extract composition showed inhibition of albumin glycation at 50 ug/ml, with #1 showing the overall best inhibitory activity. Aminoguanidine (AG) (1 mM) had good inhibitory activity, which is its known activity.

Example 2

Anti-Glycation Activity

Normal human dermal fibroblasts (NHDF) were cultivated in conditions that allow the synthesis of high amounts of extracellular matrix (ECM). NHDF were grown to confluence in normal medium in adequate format. Vitamin C was added to the media to induce matrix synthesis/deposition Cells were treated, (or not treated for the negative control) by three concentrations of the mineral extract composition or by a reference compound for a positive control (aminoguanidine). All the conditions were performed in triplicate.

An excess of glucose was added to die cells and the cells were incubated at 37° C. for 15 days. At the end of the time, ECM proteins (mainly collagen) were extracted and purified and a fraction of each sample was loaded onto nitrocellulose in reproducible spots.

The introduction of AGEs in collagen was shown using an anti-AGE antibody and it was labeled using a peroxidase conjugate and chemiluminescent reaction (ECL). Relative signal qualification was performed using a chemiluminescense imager.

The results are illustrated below in Tables 1 and 2.

TABLE 1

| First membrane Treatment | Conc. | Intensity (AU) | Average | Sem | % Control |
|---|---|---|---|---|---|
| Control |  | 49908 | 53561 | 1843 | 100 |
|  |  | 54965 |  |  |  |
|  |  | 55809 |  |  |  |
| Aminoguanidine | 1 mg/ml | 24719 | 33454 | 4377 | 62 |
|  |  | 38328 |  |  |  |
|  |  | 37316 |  |  |  |
| Mineral Extract Composition 1 | 0.1 µg/ml | 46270 | 42886 | 2991 | 80 |
|  |  | 45465 |  |  |  |
|  |  | 36922 |  |  |  |
|  | 25 µg/ml | 48675 | 51128 | 6560 | 95 |
|  |  | 63517 |  |  |  |
|  |  | 41193 |  |  |  |
|  | 250 µg/ml | 38893 | 44343 | 2755 | 83 |
|  |  | 47772 |  |  |  |
|  |  | 46363 |  |  |  |
| Mineral Extract Composition 2 | 0.1 µg/ml | 48856 | 48340 | 1823 | 90 |
|  |  | 51209 |  |  |  |
|  |  | 44956 |  |  |  |

TABLE 1-continued

| First membrane Treatment | Conc. | Intensity (AU) | Average | Sem | % Control |
|---|---|---|---|---|---|
| | 25 µg/ml | 51233 | 44177 | 3658 | 82 |
| | | 38977 | | | |
| | | 42322 | | | |
| | 250 µg/ml | 43883 | 40454 | 3144 | 76 |
| | | 43304 | | | |
| | | 34176 | | | |
| Mineral Extract Composition 3 | 0.1 µg/ml | 40338 | 45520 | 3833 | 85 |
| | | 53004 | | | |
| | | 43219 | | | |
| | 25 µg/ml | 46324 | 45936 | 1593 | 86 |
| | | 48480 | | | |
| | | 43003 | | | |
| | 250 µg/ml | 37197 | 41239 | 2569 | 77 |
| | | 46008 | | | |
| | | 40513 | | | |
| Mineral Extract Composition 4 | 0.1 µg/ml | 34161 | 42089 | 4034 | 79 |
| | | 47349 | | | |
| | | 44758 | | | |
| | 25 µg/ml | 43224 | 50402 | 7095 | 94 |
| | | 64592 | | | |
| | | 43389 | | | |
| | 250 µg/ml | 44930 | 42543 | 4084 | 79 |
| | | 48115 | | | |
| | | 34585 | | | | sem: standard error of the mean
AU: arbituary unit

TABLE 2

| Membrane 2 Treatment | Conc | Intensity (AU) | Average | Sem | % Control |
|---|---|---|---|---|---|
| Control | | 53903 | 60294 | 4067 | 100 |
| | | 59133 | | | |
| | | 67846 | | | |
| Aminoguanidine | 1 mg/ml | 36460 | 38752 | 1414 | 64 |
| | | 38464 | | | |
| | | 41333 | | | |
| Control | | 53903 | 60294 | 4067 | 100 |
| | | 59133 | | | |
| | | 67846 | | | |
| Aminoguanidine | 1 mg/ml | 36460 | 38752 | 1414 | 64 |
| | | 38464 | | | |
| | | 41333 | | | |
| Mineral Extract Composition 5 | 0.1 µg/ml | 38940 | 45072 | 3066 | 75 |
| | | 48090 | | | |
| | | 48186 | | | |
| | 25 µg/ml | 52306 | 56723 | 2224 | 94 |
| | | 58468 | | | |
| | | 59394 | | | |
| | 250 µg/ml | 50460 | 51318 | 439 | 85 |
| | | 51585 | | | |
| | | 51908 | | | |
| Mineral Extract Composition 6 | 50 µg/ml | 40393 | 46127 | 3053 | 77 |
| | | 47176 | | | |
| | | 50811 | | | |
| | 200 µg/ml | 36099 | 45666 | 5859 | 76 |
| | | 44590 | | | |
| | | 56308 | | | |
| | 500 µg/ml | 44656 | 50828 | 3314 | 84 |
| | | 51825 | | | |
| | | 56004 | | | | sem: standard error of the mean
AU: arbituary unit

The mineral extract compositions showed a tendency to decrease the production of the end product of glycation (AGE).

Example 3

The objective of this assay was to test the effect of mineral extract compositions (6 lots) cm the mitochondrial metabolism m a cell culture population, using MTT assay. MTT assay measures the activity of succinate dehydrogenase, a key enzyme in the respiratory electron transport chain in mitochondria (Berridge & Tan, 1993).

Methods

Mineral extract compositions were diluted in type I sterile water to 10 mg/ml, sterilized by 0.22 micron filtration and incubated at dilutions 500 ug/ml, 50 ug/ml and 5 ug/ml and 0.5 ug/ml with 2,500 human dermal fibroblasts from an 81 year old female donor (Cascade Biologics, lot #061215-901) per well for 72 h in high glucose DMEM medium with 2.5% calf serum.

For mitochondrial metabolism measurement at the end of the experiment, MTT (3-(4,5-dimethylthiazol-2-yl)-2,5-diphenyltetrazolium bromide, Sigma cat. #M 5655) was added to cell cultures and incubated for 2 h. Culture media were then discarded and intracellular MTT reduction product formazan was solubilized in 100% DMSO. The colorimetric signal proportional to the mitochondrial activity in the cell cultures was measured with the BioRad microplate spectrophotometer 3550-UV at 570 nm.

For cell number measurement, at the end of the experiment, cytoskeletal proteins were stained with sulforhodamine B and the colorimetric signal proportional to cell numbers measured with the BioRad microplate spectrophotometer 3550-UV at 570 nm.

The mitochondrial metabolism was standardized with regard to cell numbers by establishing the ratio of the two corresponding signals.

Results and Discussion

Figure 2A:
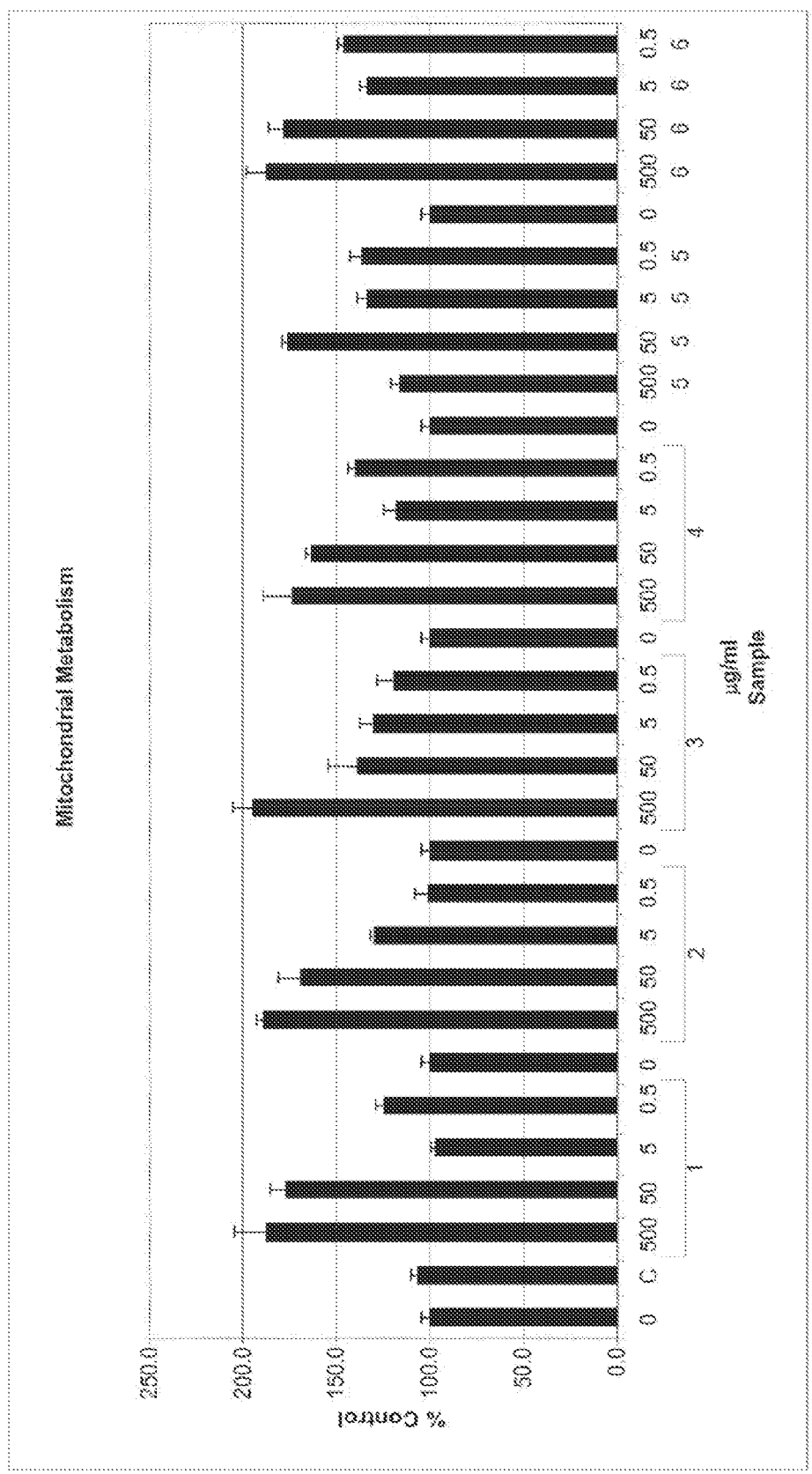
FIGS. 2A and B are graphs showing the effects of mineral extract composition on mitochondrial metabolism. A: increase of the mitochondrial activity in total cell population, B: increase of the mitochondrial activity on a per cell basis.

See FIG. 2A and B for results. All mineral extract compositions lots tested exhibited similar pattern, with one (#2) stimulating mitochondrial metabolism up to nearly 100% over the baseline. See. FIG. 2A. 0 is the negative control where water was added to the cells, and each of six samples of mineral extract composition, labeled 1-6. m 500 ug/ml, 50 ug/ml and 5 ug/ml and 0.5 ug/ml concentration for each of the 6 samples. C is creatine, added to the cells at 500 ug/ml.

Figure 2B:
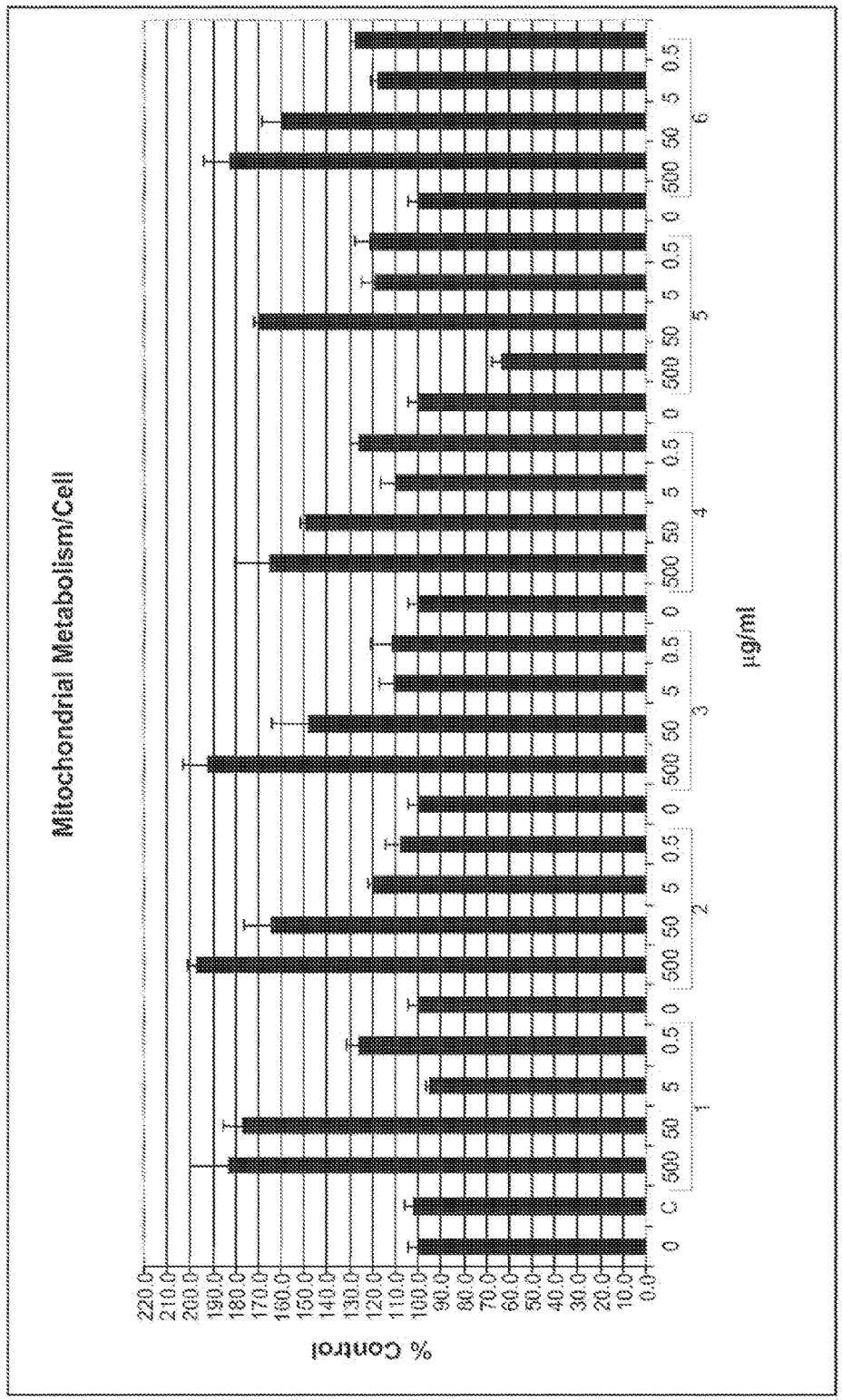

Interestingly, the dermal fibroblasts from an elderly donor were only marginally sensitive to creatine (6.3% stimulation), and were not sensitive to basic fibroblast growth factor (bFGF, results not shown). Furthermore, importantly, mineral extract compositions did not stimulate cell proliferation in the assay, just the metabolism. See FIG. 2B.

Example 4

Collagen secreted by dermal fibroblasts is a major component of the extracellular matrix in the skin. In aged and photodamaged skin, the new collagen pool is decreased due to the inferior amount and quality of dermal fibroblasts. The object of this project was to test the mineral extract composition on type I collagen levels in human dermal fibroblast conditioned medium.

Methods

Normal human dermal fibroblasts (passage 7, lot #7F1254, Cambrex, Walkersville, Md.) were seeded in a 96-well plate (plate #431) in DMEM medium (high glucose) containing 5% fetal calf serum, and grown to late subconfluent stage. Aqueous solutions of mineral extract composition were prepared in sterile Type I water and added to cell cultures at 1/20 dilution. Water was the non-treated control and magnesium ascorbyl phosphate (MAP cat. #A8960, Sigma, St. Louis, Mo.) was the positive control. Cell culture conditioned media were harvested 5 days after the start of the experiment and tested for type I collagen by sandwich ELISA using affinity-purified antibodies, followed by streptavidin-avidin-HRP conjugate and ABTS, according to standard ELISA protocol (Dobak et al., 1994, Zhao et al, 2005).

Figure 3:
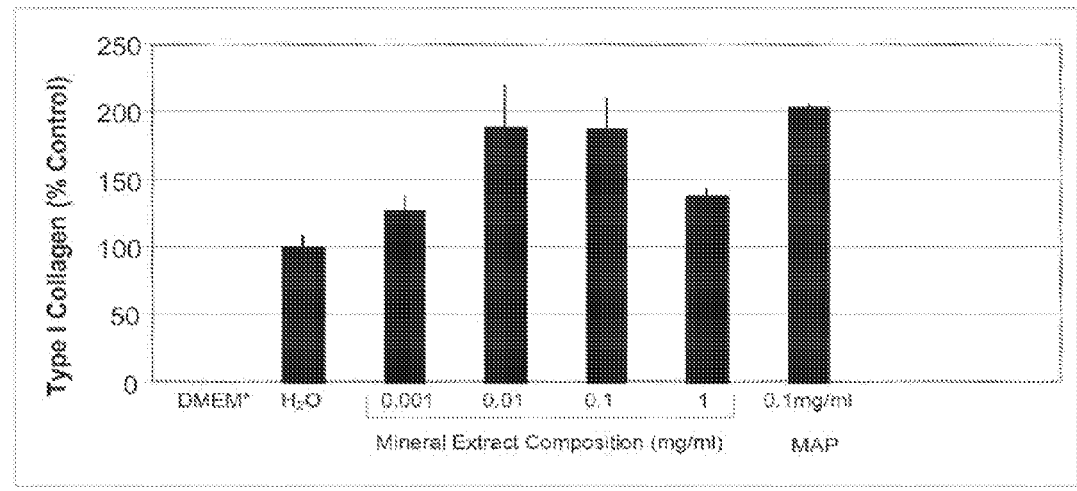
FIG. 3 is a graph showing the effect of a mineral extract composition on type I collagen production by human cells

The colorimetric signal proportional to collagen content was measured with the BioRad microplate spectrophotometer 3550-UV at 405 nm. See FIG. 3, Effect of mineral extract composition on type I collagen in HDF-conditioned medium.

Result and Discussion

Strong stimulation of collagen I was seen for the positive control (MAP). See FIG. 3. The mineral extract composition showed an excellent, bell-shape stimulation of type I collagen up to nearly 90% above the non-treated (water) control, comparable with the positive control (MAP). The bell shape of the dose-response curve may indicate that the optimal concentration of the mineral extract composition for type I collagen stimulation is between 0.01 and 0.1 mg/ml (0.1-1%).

Example 5

Metalloproteinase (MP) (collagenase) activity was measured with Enzcheck kit from Molecular Probes (Invitrogen, IL) using quenched fluorescent gelatin and Clostridium collagenase IV, a generic metalloproteinase. Mineral extract composition, in dilutions of 500 ug/ml, 50 ug/ml and 5 ug/ml and 0.5 ug/ml, were incubated in the presence of collagenase substrate-quenched fluorescin-linked gelatin and in the presence of the proteolytic enzyme collagenase. Phenanthroline, a potent MP inhibitor was used as positive control at 100 ug/ml. The kinetics of the release of the digested, fluorescent gelatin were measured at excitation/emission wavelengths of 485/530 nm with Millipore Cytofluor 2350 microfluorometer.

Results and Discussion

Figure 4:
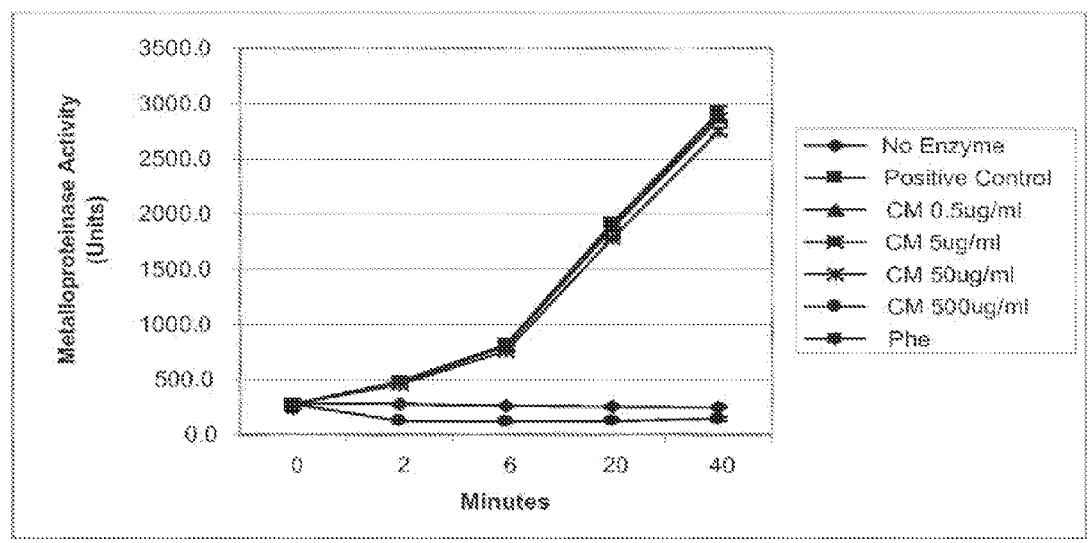
FIG. 4 is a graph showing the activity of mineral extract composition on metalloproteinase activity, in vitro.

As illustrated in FIG. 4, the mineral extract composition has metalloproteinase-inhibitory activity. This activity can be detected at concentrations as low as 50 ug/ml (6% inhibition) and it is 100% at 500 ug/ml. As expected, MP activity was totally inhibited by phenanthroline.

Most metalloproteinase inhibitors are indiscriminate bivalent cation chelators. The mineral extract composition may act through a different mechanism of action. It is worth investigation whether this potentially novel mechanism of action impairs specificity for a subset of metalloproteinases, which would be of interest for dermatological applications.

Example 6

The mineral extract composition was tested for its antioxidant effect in an independent in vitro study to assess the Oxygen Radical Absorbance Capacity (ORAC Score), using a standard fluorescent assay technique.

The leading antioxidant fruits have been reported to have ORAC scores in the range of 15-30, which is quite significant antioxidant capacity, The mineral extract composition samples, tested using the same protocol was found to have between 10-30 times greater ORAC scores than the leading antioxidant fruits on an equivalent weight basis.

| ORAC Value of Fruits (μmole TE/g) | |
|---|---|
| Cherry | 15 |
| Strawberry | 24 |
| Raspberry | 28 |
| Blackberry | 28 |
| Blueberry | 28 |
| Pomegranate | 32 |

Oxygen Radical Absorbance Capacity of Mineral Extract Composition

Because of its damaging effect on vital biological systems, oxidative stress has been implicated in more than 100 diseases and aging (Ames et al., 1993). The objective of this test was to measure the antioxidant potential of several samples of mineral extract composition using oxygen radical absorbance capacity (ORAC) assay.

Methods

ORAC assay was performed according to the method described by Ou et al. (2001), with minor modifications (Sunny BioDiscovery Protocol #21). The ORAC assay measures the ability of antioxidant components to inhibit the decline in disodium fluorescein (FL) (Sigma-Aldrich, St Louis, Mo.) fluorescence that is induced by the peroxyl radical generator, 2',2'-Azobis (2-amidinopropane) dihydrochloride (AAPH) (Wako Chemicals, Richmond, Va.).

Samples of mineral extract compositions were diluted in type I sterile water to 10 mg/ml, sterilized by 0.22 micron filtration and added at 10 ug/ml to reaction mixtures. Trolox (freshly prepared in type I water) at concentrations 1 ug/ml, 5 ug/ml and 10 ug/ml was used for the generation of standard curve, by plotting the Area Under the Curve (AUG) calculated with the NIH ImageJ software, against Trolox concentrations expressed in micromoles/liter. AUC for each sample was then applied to the Trolox standard curve. See Table 3.

TABLE 3

| ORAC Values | |
|---|---|
| Mineral Extract Composition (sample no.) | Antioxidant Activity (μmoles TE/g) |
| 1 | 1000 |
| 2 | 925 |
| 3 | 1400 |
| 4 | 925 |

Example 7

An Anti-Glycation Composition

An anti-glycation composition comprising
Fresh Orange Juice 98-80% (weight percent)
Potassium Sorbate 0.15%
Vitamin E (Tocopherol) 0.05%
Dry Mineral Extract Composition of Table 1 1.00%
Procedure
 1. Using suitable press equipment, squeeze orange juice
 2. Add and mix its Potassium Sorbate and Tocopherol
 3. Add and mix Mineral Extract Composition
 4. Pack and chill at 5-8 degree, C.

Mineral content of one liter of Processed Orange Juice delivers no less than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium. Fluorine, Gadolinium, Gold, Hafnium, Holmium, Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium. Tin, Titanium, Tungsten, Vanadium, Ytterbium, Yttrium, Zinc, Zirconium.

Example 8

Beverage Additive-Powdered Concentrate Mineral Pack

Package 7 g of the dry mineral extract composition of Table I in foil pack. Mixing the 7 g of dry mineral extract composition in the foil pack into 12 ounces of any beverage including water delivers no teas than one ppm of Macro Minerals consisting of a blend of Calcium, Chlorine, Magnesium, Manganese, Phosphorous, Potassium, Silicon, Sodium, and no less that 0.0001 ppm of Micro Minerals consisting of a blend of Aluminum, Antimony, Arsenic, Barium, Beryllium, Bismuth, Boron, Bromine, Cadmium, Cerium, Cesium, Chromium, Cobalt, Copper, Dysprosium, Erbium, Europium, Fluorine, Gadolinium, Gold, Hafnium, Holmium. Iodine, Indium, Iridium, Iron, Lanthanum, Lead, Lithium, Lutetium, Mercury, Molybdenum, Neodymium, Nickel, Niobium, Palladium, Platinum, Praseodymium, Rhenium, Rhodium, Rubidium, Ruthenium, Samarium, Scandium, Selenium, Silver, Strontium, Sulfur, Tantalum, Terbium, Tellurium, Thallium, Thorium, Thulium, Tin, Titanium, Tungsten, Vanadium, Ytterbium, Yttrium. Zinc, Zirconium.

Example 9

Effect of a Mogroside/Mineral Extract Composition and its Components on Type I Collagen A mogroside/mineral extract composition is made by combining a 3% liquid mineral extract composition at about 84% w/w % with citric acid (0.01% w/w %) and preservatives (at least 0.01% w/w %) and di- and tripeptides from casein hydrolysate (1.0% w/w %). This mixture is combined wife soluble dietary fiber (1.50% w/w %) and modified food starch (1.60% w/w %). This mixture is mixed with sorbitol solution, 70% USP/FCC (9.0% w/w %) and powdered mogrosides (luo han guo fruit extract) (MB North America) (3.0 % w/w %). This mixture is combined with Flavor, (0.5% w/w %*. Referred to herein as SS II.

Collagen is the main component of connective tissue (fascia), cartilage, ligaments, tendons, bone and teeth and it also provides structural support to blood vessels. The objective of this assay Sites to determine the effect of a mogroside/mineral extract composition and its individual components on type I collagen levels in human dermal fibroblast conditioned medium.

Methods

A mineral extract composition (TL), Lot #100-151106, ~3% Solution, and a mogroside/mineral extract composition as taught herein (SS II), mogrosides of Luo Han Quo Extract (Luo HG, Lot #MOG01-060502), Erythritol (Eryt, Lot #07241BP952) and Xylitol (Xylit, Lot #H125T7G1) were tested in the assay. All test materials were kept at room temperature. Materials were diluted in type 1 sterile water, filtered through a 0.22 µ filter and assayed at final concentrations 1%, 0.5%, 0.1% 0.05% and 0.01% v:v) for TL and SS II, and 0.5%, 0.1%, 0.05% and 0.01% (w:v) for Luo HG, Eryt and Xylit, on adult human dermal fibroblasts (aHDF, donor 58 years of age, Lonza, lot #7F39=019 breast) in high glucose DMEM with 5% calf serum. Water was the non-treated control and magnesium ascorbyl phosphate (MAP cat. #A8960, Sigma, St. Louis, Mo.) was the positive control. Cell culture conditioned media were harvested 72 h after the start of the experiment and tested for type I collagen by sandwich ELISA using affinity-purified antibodies, followed by streptavidin-avidin-HRP conjugate and ABTS, according to standard ELISA protocol (Dobak et al., 1994, Zhao et al, 2005). The colorimetric signal proportional to collagen content was measured with the BioRad microplate spectrophotometer 3550-UV at 405 nm.

Results and Discussion

Figure 5:
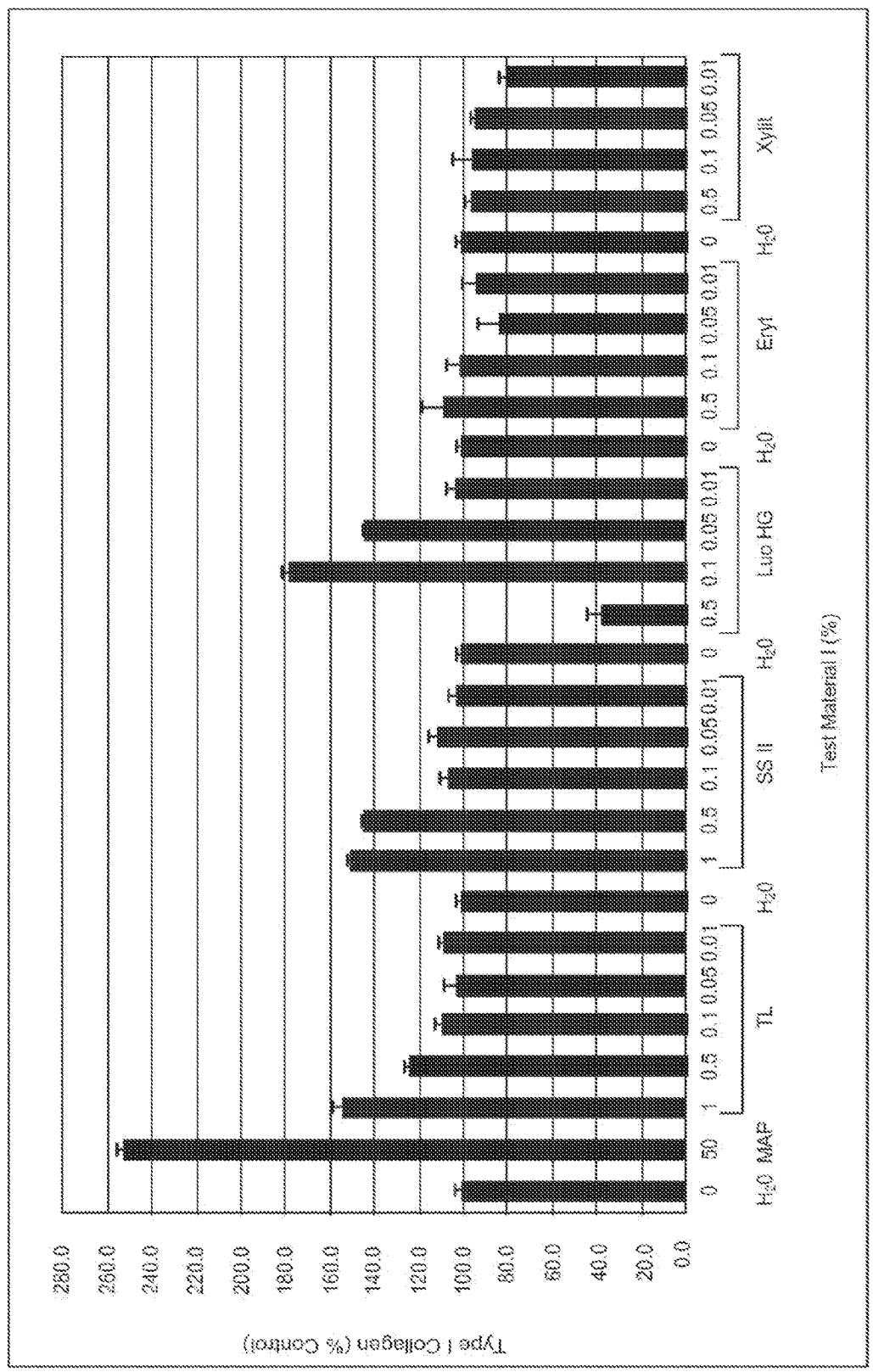
FIG. 5 is a graph showing the collagen stimulatory activity of compositions of the present invention.

As illustrated in FIG. 5, TL and SS II had a strong dose-dependant collagen-stimulatory activity at 1% and 0.5% (up to 54% for TL and 49% for SS II). Luo HG had a powerful, dose-dependant stimulatory activity at 0.1% and 0.05% up to 77%). In contrast, Erythritol and Xylitol had no significant activity at all concentrations tested. 0 is water, the non-treated control, MAP was used at 50 µg/mL, Luo HG is indicated by L in FIG. 5.

Example 10

Figure 6A:
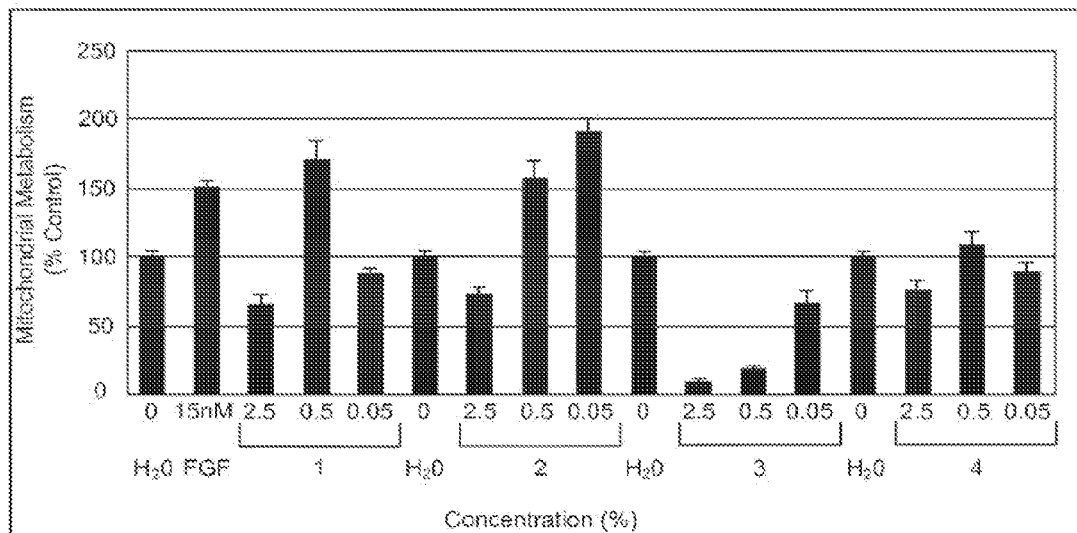
FIGS. 6A and B are graphs showing the metabolism stimulatory activity of compositions of the present invention.

Effect of a Mogroside/Mineral Extract Composition, a Mineral Extract Composition, Sucralose and Erythritol on Mitochondrial Metabolism The objective of this Example was to test the effect of 4 samples: A mogroside/mineral extract composition (Labeled-1 in FIG. 6A), mineral extract composition (Labeled-2 in FIG. 6A), Sucralose liquid concentrate (Labeled-3 in FIG. 6A) and erythritol (Labeled-4 in FIG. 6A) on the mitochondrial metabolism I fibroblast populations, using MTT assay. MTT assay measures the activity of succinate dehydrogenase, a key enzyme in the respiratory electron transport chain in mitrochondria (Berridge & Tan, 1993).

Methods

Test materials-were mogroside/mineral extract composition as made above in Example 9, mineral extract composition (~3% Solution) , Sucralose Liquid Concentrate (25% Sucralose by weight)-lot #F2304B311LB and Erythritol (25% Aqueous Solution)-lot #RFA 2104-35, and were kept at room temperature. Materials were diluted in type I sterile water, filtered through a 0.22 µ filter and assayed at final concentrations of 2.5%, 0.5% and 0.05% v:v) on human dermal fibroblasts (Invitrogen) for 72 h in high glucose DMEM medium with 5% calf serum.

In order to measure mitochondrial metabolism in whole cell populations, at the end of the experiment, MTT (3-(4,5-dimethylthiazol-2-yl)-2,5-diphenyltetrazolium bromide, Sigma cat. #5655) was added to cell cultures and incubation was continued for an additional 2 hours. Culture media were then discarded and intracellular MTT reduction product formazan was solubilized in 90% isopropanol. The colorimetric signal proportional to the mitochondrial activity in the cell cultures was measured with the BioRad microplate spectrophotometer 3550-UV at 570 nm.

Results and Discussion

Figure 6B:
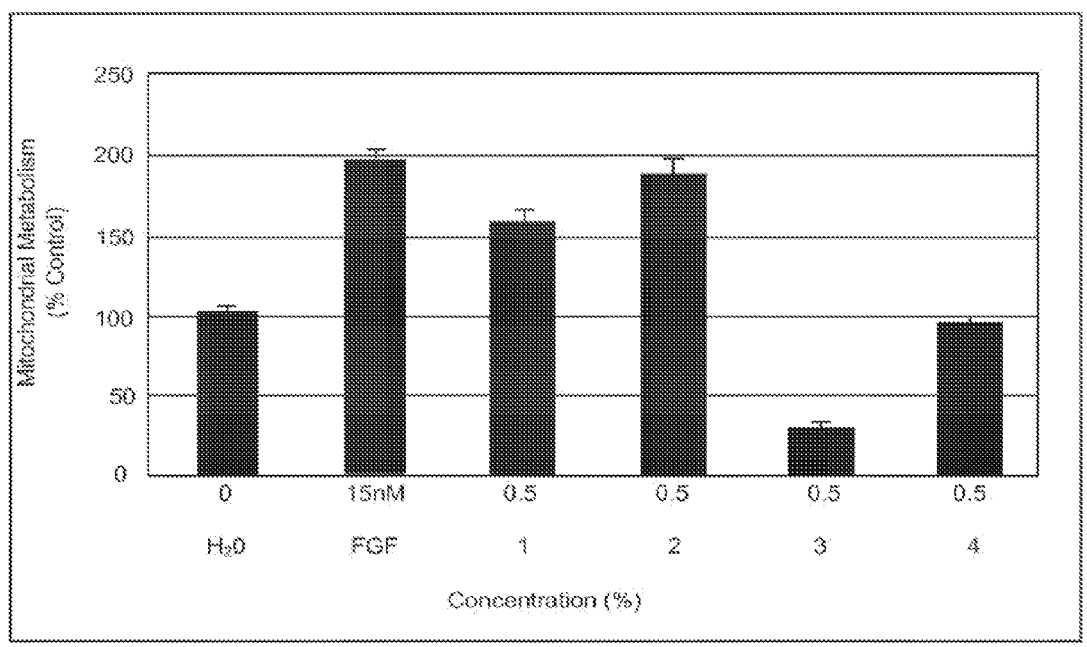

The results show that the mogroside/mineral extract composition has metabolism-stimulatory activity. The mineral extract composition had a dose-response activity, while Sucralose inhibited cell metabolism and Erythritol had no activity at tested concentrations (see FIG. 6A). The results of this first experiment (performed in quadruplicate) were further confirmed and reproduced by the repetition of one dose of each test material (see FIG. 6B). Baste Fibroblast Growth Factor (FGF at 15 nM) was used as positive control and showed metabolic stimulation, as expected. 0 represents the water, non-treated sample.

Example 11

Effect of a Mogroside/Mineral Extract Composition and its Components on Protein Glycation The Maillard Reaction (non enzymatic glycation) is a chain of reactions resulting in crosslinkage of amine groups on macromolecules such as extracellular matrix proteins in the skin with carbonyl groups on reducing sugars. These crosslinked macromolecules are called Advanced Glycation End products (AGEs). The formation of AGEs is enhanced by free radicals. It is a marker of physiopathologies such as diabetes and atherosclerosis, and is associated with aging and photoaging processes (van Boekel et al., 1991). The objective of this assay was to determine the effect of a mogroside/mineral extract composition and its individual components on AGE formation in the albumin/glucose model system.

Methods

Mineral extract composition (TL, ~3% Solution) and a mogroside/mineral extract composition (SS II), Luo Han Guo Extract (L, Lot #MOG01-060502), Erythritol (E, Lot #07J241BP952) and Xylitol (X, Lot #H125T7G1) were kept at room temperature. Materials were diluted in type I sterile water, filtered through a 0.22 µ filter and assayed at final concentration of 1%, (v:v) for TL and SS II, and 0.5%. 0.1% 0.05% and 0.01% (w:v) for L, E and X, for three weeks days at 37° C. in the presence or absence of glucose (Sigma G8270), in the medium containing 10 mg/ml of albumin and sodium azide. The positive inhibitor control was aminoguanindine hydrochloride (AG) at 1 mM, (Sigma 396494).

Protein glycation was detected by the increase of non-tryptophan fluorescence (excitation at 360 nm, envision at 460 nm) using microplate fluorometer Cytofluor 2350 (Millipore), as previously described (Argirova and Argirov, 2003). The glycation value for each experimental point was obtained by subtracting the background reading (samples without glucose) and was expressed as % of control (water).

Results and Discussion

The results show that the mineral extract composition and the mogroside/mineral extract composition have a moderate (20-25%) glycation inhibitory activity at 1% concentration and no inhibitors- activity at all other concentrations tested. Luo Han Guo extract showed a dose-dependant glycation-inhibitory effect at all concentrations tested (up to nearly 90% inhibition at 0.5%) in this model system. Xylitol had no effect and Erythritol had a moderate inhibitory effect at lower concentrations.

Figure 7:
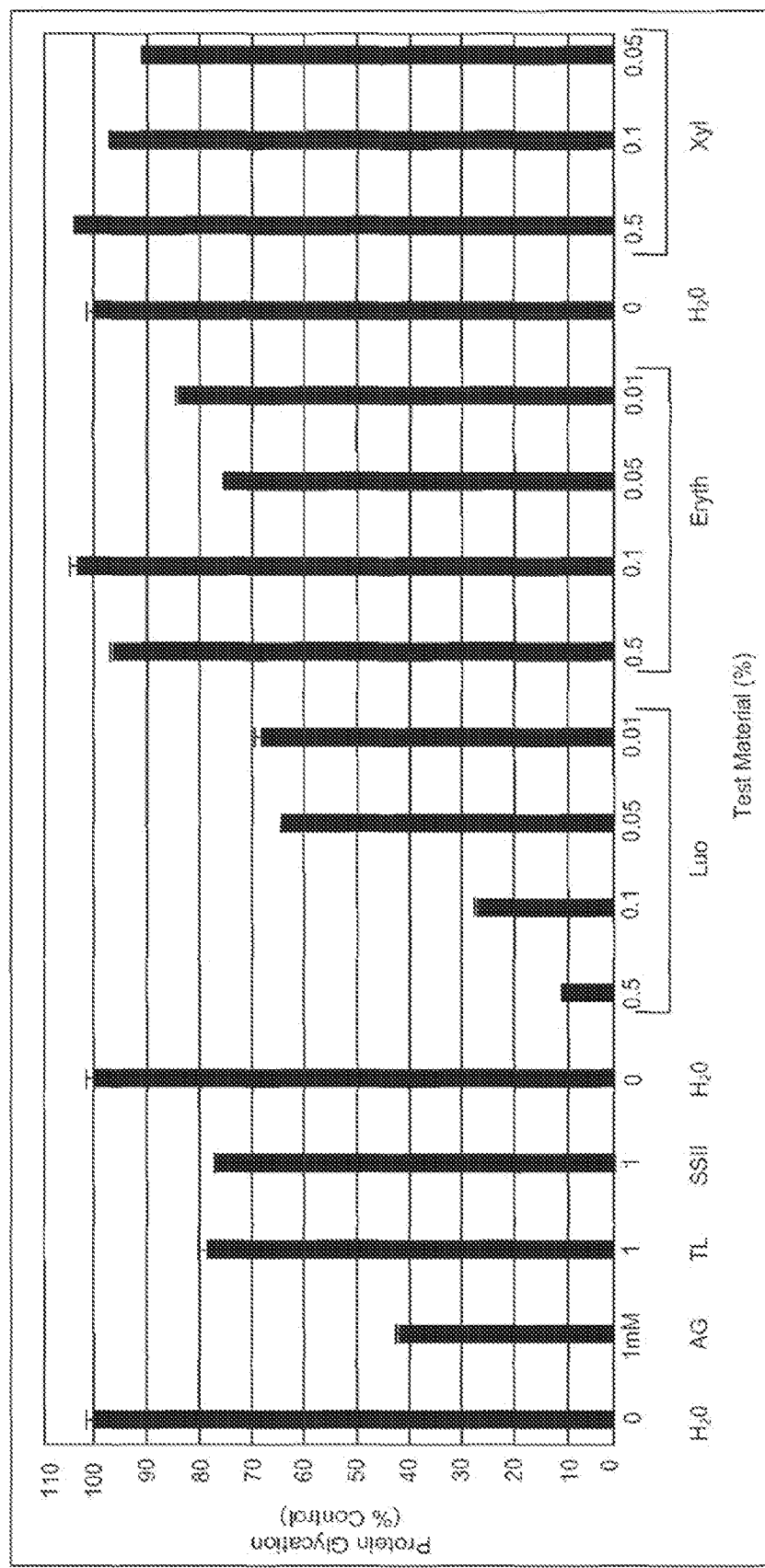
FIG. 7 is a graph showing the glycation inhibitory activity of compositions of the present invention.

Aminoguanidine (AG) showed a strong glycation-inhibitory activity demonstrating the technical success of the experiment. See FIG. 7.

Example 12

The objective of the experiment was to determine the effect of a mineral extract composition at 0.5% (v:v) on the gene expression pattern in human adult fibroblasts.

Methods

Human fibroblasts (lot #7F3019, breast donor 58 years of age) were obtained from Lonza, Inc. and cultured according to the manufacturer's instructions, mineral extract composition (Lot #100-151106) was added to confluent, established cell cultures at 0.5% (v:v) in DMEM (high glucose)/5% FCS for 48 h, in 75 cm2 flasks. Upon completion of the incubation, cells were trypsinized, pelleted, and snap frozen in liquid nitrogen. The pellets contained about 4 millions cells.

Cells were then subjected to RNA extraction with Qiagen kit. The quality of extracted RNA was assayed twice by electrophoresis (after extraction and before microarray analysis). Samples were hybridized in technical duplicates using human OneArray platform from Phalanx Biotech (Palo Alto, Calif.). The Excel file yielding information on over 30,000 probes was then further processed in-house to eliminate differences with high p values (p>0.1) and low fold change (<2). All genes described as "uncategorized" and "putative" were excluded from the final analysis. Array Studio V2.5 (Omicsoft) software was used to identify functional categories affected by the test materials.

Results and Discussion

The quantity and quality of isolated RNA was excellent as was the ratio of nucleic acids to proteins, indicating that RNA was not only intact but also free of proteinaceous contaminants. The microarray hybridization was successful. Treatment with the mineral extract composition showed variation in gene expression pattern. The mineral extract composition modulated the expression of 2914 probes, which represents about 9% of the total probes. The Array Studio analysis showed that the mineral extract composition, significantly modulated 20 functional categories of genes.

The cellular metabolism category was the most significantly modulated. For example, a consistent upregulation of precursors of mitochondrial ribosomal proteins and NADH dehydrogenases was seen, suggesting activation of mitochondrial metabolism through the upregulation of the synthesis of effectors implicated in the generation of ATP. Further indication of increased mitochondrial activity is the upregulation of cytochrome c oxidase—the terminal enzyme of the mitochondrial respiratory chain, which plays a key role in the regulation of aerobic production of energy.

Another significantly modulated Category was the one involved in sphingolipid metabolic process. An over 5 fold increase in the expression of MD-1 protein was seen. This gene/protein is involved in the synthesis of glycan glycosphingolipids, molecules that are involved with the integrity of cell membranes. Compounds benefiting this pathway may be useful for skin care applications. Other genes that were upregulated include those involved in detoxification/antioxidant activity (over 2 times stimulation of Peroxiredoxin-5 and Superoxide Dismutase—SOD-expression), inhibition of cell death (through caspase pathway inhibition) and upregulation of hyaluronic acid and type I collagen synthesis.

Example 13

A Dry Sweetener Composition

This composition is as example of sweetener comprising a mineral extract composition, Luo Han Guo Extract of mogrosides, and other ingredients to form a sweetener. See the Table below for specific amounts.

| INGREDIENTS | C.T.FA. NAME | W/W % |
|---|---|---|
| Phase A. | Phase A. | Phase A. |
| 1- Mineral Extract Powder | 1- Mineral Extract Powder | 6.00 |
| 2- Citric Acid, Anhydrous, USP, FCC | 2- Citric Acid, Anhydrous, USP, FCC | 0.20 |
| 3- Sodium Benzoate: NF, FCC | 3- Sodium Benzoate, NF, FCC | 0.20 |
| 4- Potassium Sorbate, NF, FCC | 4- Potassium Sorbate, NF, FCC | 0.20 |

-continued

| INGREDIENTS | C.T.FA. NAME | W/W % |
|---|---|---|
| 5- Nutriose FM 06 | 5- Dextrin (Soluble Dietary Fiber) | 3.50 |
| 6- N-Zorbit M | 6- Tapioca Maltodextrin | 52.90 |
| 7- Sorbogem 712 Crystalline Sorbitol NF/FCC | 7- Sorbitol, NF/FCC | 10.50 |
| 8- Luo Han Guo Fruit Concentrate | 8- *Momordica Grosvenori Swingle* Mogrosides | 5.00 |
| 9- Aerosil 200 Pharma | 9- Silica | 1.00 |
| Phase B | Phase B. | Phase B |
| 9- N-Zorbit M | 9- Tapioca Maltodextrin | 20.00 |
| 10- Flavor | 10- Flavor | 0.50 |
| | Total | 100.00 |

Additional ingredients or substitutions can be chosen from the list below.

1-Food Starch Modified, Bulking, and/or functional agents:
  Tapioca Maltodextrin.
  Wheat Dextrin
  Waxy Maize
  Tapioca Starch
  Film Formers
  Firming Agents
  Flavor Carriers
  Gelling Agents
  Grain-Based Food Ingredients
  Hydrolyzed Cereal Solids
  Maltodextrins see also Bulking Agents; Encapsulated Ingredients
  Meat Extenders
  Oils, Vegetable, Corn
  Starches, Corn, Dusting, Modified, Pregelatinized, Thin Boiling
  Tableting Agents
  Standard Stabilizing Gums such, as: Agar, Alginates, Acacia, Carrageenan, Carboxymethyl Cellulose (CMC), hydroxypropyl methylcellulose, microctystalline cellulose, and methylcellulose. Locust bean gum. Guar (endosperm of the plant Cyamopsis tetragonoloba), Inulin (occurring dietary fiber that can be extracted from the chicory root and Jerusalem artichokes), Pectin (Pectin is extracted from the peels of citrus fruit), Xantam Gum. Gum Arabic.
  Nutraceutical Ingredients: include any kind of natural, and/or synthetic ingredients which may establish a link between food and health in humans and/or animals. It may include ingredients obtained from fruits, herbs, marines, spices, vegetables and synthetically formed compounds. These groups include, yet are not limited to, the following ingredients: isoflavones, lecithin, oils and fats (low trans-fat oils), plant sterols, soy proteins, vitamins, Vitamin E, and mixed tocopherols
  Flavors: any natural and/or synthetic flavors might be incorporated into the composition. Flavor might be used in order to encourage use of composition.

What is claimed is:

1. A method of treating glycation-related conditions, comprising, administering to a human or animal an effective amount of an extracted mineral element composition wherein said extracted mineral element composition is prepared by a method consisting of:
  one acid treatment step, a settling step, a separating step, and a concentration step,
  wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
  wherein the settling step consists of allowing solids from the water-acid-soil slurry to settle;
  wherein the separating step consists of separating the liquid of the water-acid-soil slurry from the settled solids wherein the solids comprise substantially all of the silica and aluminum from the clay soil, mixture of clay soils, or a mixture of clay soils and leonardite;
  wherein the concentrating step consists of concentrating the separated liquid to form a liquid extracted mineral element composition comprising (i) calcium, chlorine, magnesium, manganese, phosphorous, potassium, silicon, and sodium, and (ii) a lower amount of silica and aluminum than the clay soil, a mixture of clay soils, or a mixture of clay soils and leonardite; and
  wherein the amount is effective in reducing at least a portion of the glycation events in a human or animal.

2. The method of claim 1, wherein the composition further comprises a sweetener.

3. The method of claim 1, wherein the composition further comprises a foodstuff

4. The method of claim 1, wherein the composition further comprises a beverage.

5. The method of claim 1, wherein the glycation-related conditions comprise formation of glycation end products, AGE formation, glycation reactions of proteins, lipids and/or nucleic acids, aging effects related to glycation reactions, and complications of diabetes, rheumatoid arthritis, Alzheimer's disease, uremia, neurotoxicity, atherosclerosis, inflammatory reactions, ventricular hypertrophy, angiopathy, myocarditis, nephritis, arthritis, glomerulonephritis, microangiopathies, and renal insufficiency, or accumulation of glycation products.

6. A method of inhibiting glycation reactions, comprising,
  a) providing an effective amount of an extracted mineral element composition wherein said extracted mineral element composition is prepared by a method consisting of: one acid treatment step, a settling step, a separating step, and a concentration step,
  wherein the one acid treatment step consists of admixing a clay soil, a mixture of clay soils, or a mixture of clay soils and leonardite with water in an amount at least two times the weight of the soil and an acid to produce a water-acid-soil slurry, wherein the amount of acid is 0.25% to 7.5% of the weight of the water;
  wherein the settling step consists of allowing solids from the water-acid-soil slurry to settle;
  wherein the separating step consists of separating the liquid of the water-acid-soil slurry from the settled solids wherein the solids comprise substantially all of the silica and aluminum from the clay soil, mixture of clay soils, or a mixture of clay soils and leonardite; and
  wherein the concentrating step consists of concentrating the separated liquid to form a liquid extracted mineral element composition comprising (i) calcium, chlorine, magnesium, manganese, phosphorous, potassium, silicon, and sodium, and (ii) a lower amount of silica and aluminum than the clay soil, a mixture of clay soils, or a mixture of clay soils and leonardite, and
  b) inhibiting a glycation reaction.

7. The method of claim 6, wherein the composition further comprises a sweetener.

8. The method of claim 6, wherein the composition further comprises a foodstuff.

9. The method of claim 6, wherein the composition further comprises a beverage.

10. The method of claim 6, wherein the composition is provided in vivo to a human or animal.

11. The method of claim 6, wherein the composition is provided in vitro.

12. The method of claim 6, wherein the composition further comprises a supplement.

13. The method of claim 6, wherein the composition further comprises botanicals.

* * * * *